United States Patent
Weisfeldt et al.

(10) Patent No.: US 8,571,663 B2
(45) Date of Patent: Oct. 29, 2013

(54) PORTABLE NEGATIVE PRESSURE VENTILATION DEVICE AND METHODS AND SOFTWARE RELATED THERETO

(75) Inventors: Myron Weisfeldt, Baltimore, MD (US); Soumyadipta Acharya, Baltimore, MD (US); Courtney C. Haswell, Morrisville, NC (US); Hargun S. Khanna, San Jose, CA (US); Yun Long, Stanford, CA (US); Vanessa C. Pau, Minneapolis, MN (US); Girish K. Singhal, Baltimore, MD (US); Nimra Taqi, Brookline, MA (US); Lu Zhao, Hangzhou (CN)

(73) Assignee: The Johns Hopkins University, Baltimore, MD (US)

(*) Notice: Subject to any disclaimer, the term of this patent is extended or adjusted under 35 U.S.C. 154(b) by 375 days.

(21) Appl. No.: 12/990,738

(22) PCT Filed: May 4, 2009

(86) PCT No.: PCT/US2009/002786
§ 371 (c)(1),
(2), (4) Date: Apr. 15, 2011

(87) PCT Pub. No.: WO2009/134459
PCT Pub. Date: Nov. 5, 2009

(65) Prior Publication Data
US 2011/0190845 A1    Aug. 4, 2011

Related U.S. Application Data

(60) Provisional application No. 61/126,237, filed on May 2, 2008.

(51) Int. Cl.
A61N 1/36    (2006.01)

(52) U.S. Cl.
USPC .............................................. 607/42; 607/62

(58) Field of Classification Search
USPC .................... 307/42; 607/20, 42, 48, 62, 115
See application file for complete search history.

(56) References Cited

U.S. PATENT DOCUMENTS

| | | | |
|---|---|---|---|
| 6,360,740 B1 | 3/2002 | Ward et al. | |
| 6,463,327 B1 | 10/2002 | Lurie et al. | |
| 7,174,891 B2 | 2/2007 | Lurie et al. | |
| 2002/0143278 A1 | 10/2002 | Bystrom et al. | |
| 2005/0085799 A1 | 4/2005 | Luria et al. | |
| 2008/0147146 A1* | 6/2008 | Wahlgren et al. | 607/61 |

* cited by examiner

*Primary Examiner* — Christopher D Koharski
*Assistant Examiner* — Jeremiah Kimball
(74) *Attorney, Agent, or Firm* — Edwards Wildman Palmer LLP; Peter F. Corless; Richard B. Emmons

(57) ABSTRACT

Featured is an apparatus an apparatus including a monitoring and sensing means, an electrode patch and a control device operably coupled to each of the sensing means and the electrodes and outputs signals to the electrodes for purposes of stimulating the phrenic nerve to thereby cause breathing by natural contraction of the diaphragm. The control device is configured and arranged to initially localize the phrenic nerve with respect to a given set of electrodes that is effective, when appropriately energized, for stimulating the phrenic nerve to establish negative pressure induced respiration in the body, based on the output signal(s) from the monitoring and sensing means. After such initially localizing; the control device thereafter repetitively outputs stimulation signals via the given set of electrodes so as to thereby continuously stimulate negative pressure induced respiration. Also featured are methods related thereto.

20 Claims, 20 Drawing Sheets

FIG. 2B

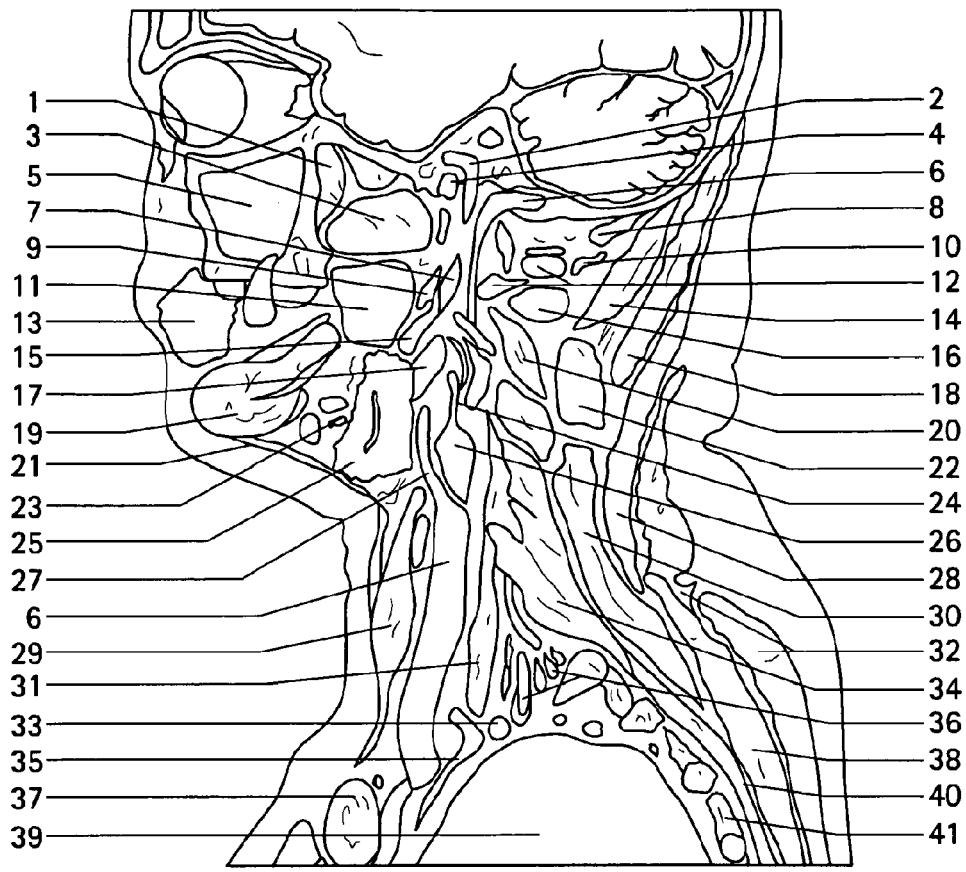

1. Temporal muscle
2. Internal corotid artery (syphon)
3. Lateral pterygoid muscle
4. Pharyngotympanic tube (auditory tube)
5. Maxillary sinus
6. Internal jugular vein
7. Styloid process
8. Rectus capitis posterior minor muscle
9. Parotid gland
10. Deep cervical veins
11. Medial pterygoid muscle
12. Atlas (transverse process)
13. Buccinator muscle
14. Rectus capitis posterior major muscle
15. Stylohyoid muscle
16. Obliquus capitis muscle
17. Digastric muscle
18. Semispinalis capitis muscle
19. Mandible
20. Lavator scapulae muscle
21. Platysma
22. Semispinalis cervicis muscle
23. Facial vein
24. External carotid artery
25. Submandibular gland
26. Common carotid artery
27. External jugular vein
28. Splenius capitis muscle
29. Sternocleidomastoid muscle
30. Semispinalis cervicis muscle
31. Scalenus medius muscle
32. Trapezius muscle
33. Subclavian artery (left)
34. Scalenus posterior muscle
35. Subclavian vein (left)
36. Brachial plexus
37. Clavicle
38. Rhomboid (major and minor) muscle
39. Lung (left)
40. Multifidus muscle
41. Interspinalis muscle

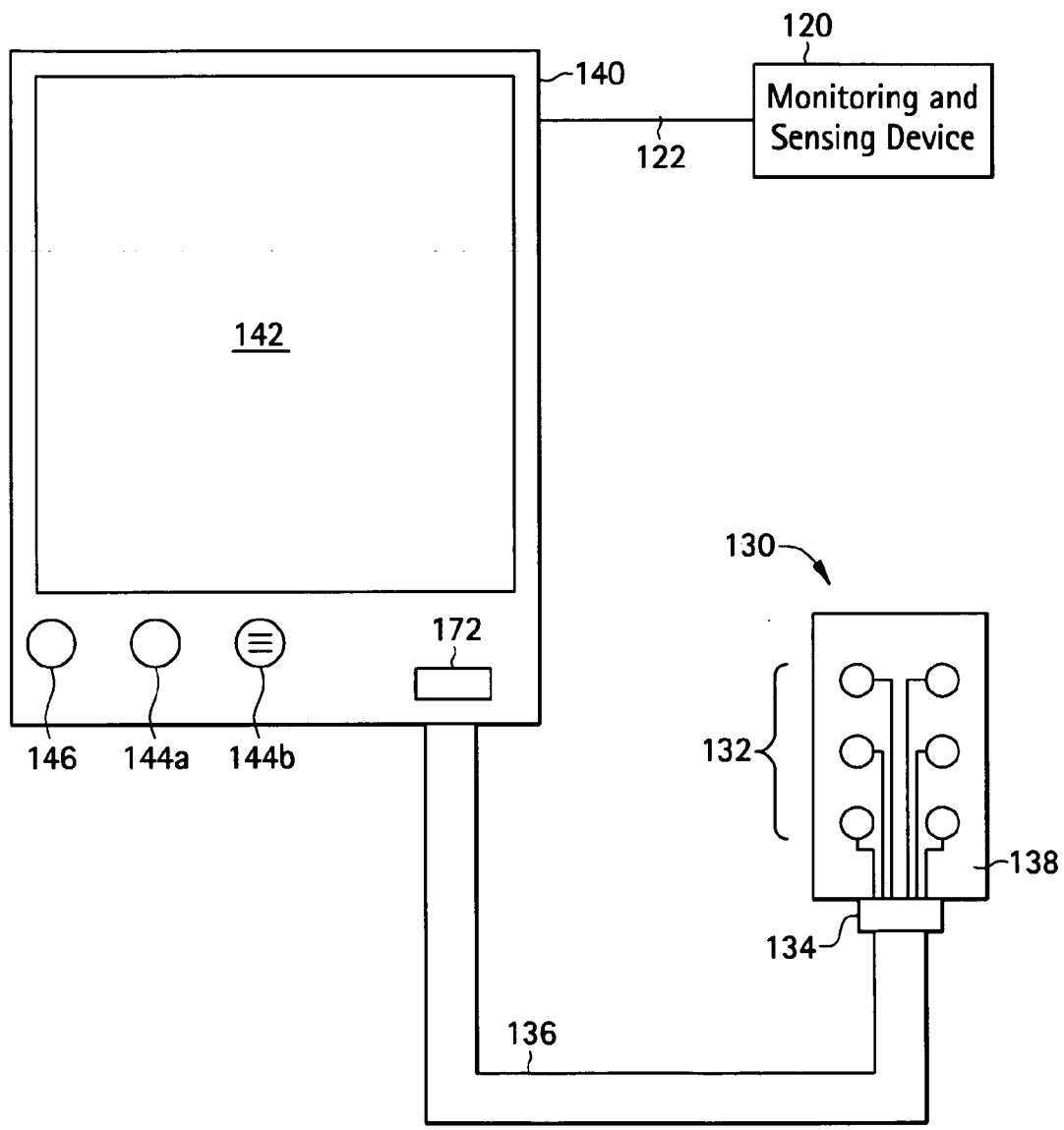

PORTABLE NEGATIVE PRESSURE VENTILATION DEVICE AND METHODS AND SOFTWARE RELATED THERETO

RELATED APPLICATIONS

This application is a 35 U.S.C. §371 U.S. national entry of International Application PCT/US2009/002786 (WO 2009/134459) having an International filing date of May 4, 2009 which claims the benefit of U.S. Provisional Application Ser. No. 61/126,237 filed May 2, 2008, the teachings of which are incorporated herein by reference.

FIELD OF INVENTION

The present invention relates to devices, systems and apparatuses for ventilating a patient, more particularly devices, systems and apparatuses that ventilate by inducing a negative pressure condition, and more specifically, devices, systems and apparatuses that are portable and that establish such a negative pressure condition by stimulation of the phrenic nerve.

BACKGROUND OF THE INVENTION

In natural breathing, the diaphragm contracts and flattens, and external intercostal muscles contract to lift the ribcage up and outward. These two processes expand the volume of the thoracic cavity, thereby inducing a decrease in intrathoracic pressure (i.e., induces negative pressure within the cavity). As a result, air flows from the atmosphere into the lungs due to the induced negative pressure within the cavity. This phenomenon is called Negative Pressure Ventilation (NPV).

When the brain is unable to transmit electrical signals, such as in the case of traumatic injuries, normal breathing stops and artificial forms of ventilation are used to resuscitate patients. The current standard for assisted ventilation during resuscitation is a form of Positive Pressure Ventilation (PPV) whereby air is pushed into the lungs through mouth-to-mouth breathing or through an endotracheal tube. Such devices include for example, a bag valve mask (typical part of a crash or ambulance kit) and mechanical ventilators whereby compressed oxygen/air is delivered pneumatically through nasal intubation or tracheotomy (e.g., see FIG. 1). In the mouth-to-mouth breathing technique an impedance threshold valve (ITV) may be used, which prevents air from entering the lungs during the decompression phase of CPR.

As PPV increases the pressure in the patient's airways, the resultant increased intra-thoracic pressure has been shown to have many detrimental hemodynamic effects such as decreased venous return and decreased cardiac output. It also has been found that PPV also can result in increased intra-luminal central venous pressure and increased intracranial pressure. The increased intracranial pressure ultimately leads to decreased cerebral perfusion pressure and decreased blood flow to the brain.

Ample clinical studies suggest that it is the hours immediately following trauma, in particular, where use of PPV has the strongest likelihood of brain damage. For example, in the United States alone, 1.5 million Americans suffer from traumatic brain injuries every year. Among these patients, increased intracranial pressure in the hours immediately following trauma accounts for 50% of deaths.

In U.S. Pat. No. 2,532,788, there are found methods and devices for stimulating a physiological functions of an individual, more specifically, for inducing of respiration. As indicated therein, prior techniques for inducing respiration included using the PPV technique or by enclosing the entire body or chest with the exception of the head and neck within an enclosure (i.e., iron-lung) and cyclically pressurizing the enclosure (resulting chest movement simulates natural breathing).

The methodology described in this patent includes placing a probe within the body so it is in physical contact with the sheath of the phrenic nerve. In this way, electrical potential applied to the probe, in the form of pulses, stimulates the phrenic nerve causing movement of the diaphragm as would occur in natural breathing. In another technique, a pair of electrodes are located on the neck so that one electrode is applied to the skin overlying the course of the phrenic nerve so that the electrical potential is applied to the nerve trunk through the skin. The second electrode is placed on the back of the neck, so that the resultant path of the current includes a portion of the phrenic nerve or one of its anatomical roots.

An anatomical view of the neck highlighting the location of one of the phrenic nerves in the neck is shown in FIG. 2. The phrenic nerve is made up mostly of motor nerve fibers for producing contractions of the diaphragm. It also provided sensory innervation for many components of the mediastinum and pleura, as well as the upper abdomen, especially the liver and the gall bladder.

As is known to those skilled in the art, phrenic nerve pacing (PNP) or diaphragm pacing (earlier referred to as electrophrenic respiration) was developed, in which electrical pulses are rhythmically applied to the diaphragm thereby causing respiration for patients that otherwise would be dependent upon a mechanical ventilator. In this technique, surgery is performed so as to place an electrode around and in physical contact with the phrenic nerve either in the neck (cervically) or in the chest (thoracically). The electrode is connected to a RF receiver implanted under the skin and an external transmitter sends RF signals to the receiver. Such devices generally fall under the category of a Class III medical device such as a pacemaker.

It thus would be desirable to provide a portable device/apparatus for stimulating one or both of the phrenic nerves so that a trauma patient can breathe by natural contraction of the diaphragm, avoiding traditional positive pressure ventilation that result in negative hemodynamic effects. Also featured are methods for localizing the phrenic nerve and inducing negative pressure respiration in such a trauma patient. It would be particularly desirable to provide such a device and method that would be minimally invasive particularly in comparison to prior art devices. Such devices/apparatuses preferably would be deployable in field emergency settings and work well with existing EMT protocols and equipment.

SUMMARY OF THE INVENTION

In broadest aspect, the present invention features an apparatus including a monitoring and sensing means, at least one electrode patch and a control device operably coupled to each of the sensing means and the electrodes. The control device outputs signals to the electrodes of the at least one electrode patch for purposes of stimulating the phrenic nerve to thereby cause breathing by natural contraction of the diaphragm. More particularly, the electrodes stimulate at least one of the two phrenic nerves in the human neck.

As described herein, in alternative embodiments, such an apparatus includes at least one deep flexible electrode in lieu of, or in addition to, the at least one electrode patch. Each of the at least one a deep flexible electrode is configured and arranged for insertion into the skin and to stimulate the phrenic nerve when such an electrode is appropriately activated or energized.

The control device also is configured and arranged to initially localize the phrenic nerve with respect to a given set of electrodes of the at least one electrode patch that is effective, when appropriately energized, for stimulating the phrenic nerve to establish negative pressure induced respiration in the body, based on the output signal(s) from the monitoring and sensing means. After such initially localizing; the control device thereafter repetitively outputs stimulation signals via the given set of electrodes so as to thereby continuously stimulate negative pressure induced respiration. In other words, the control device initially goes through a localizing mode of operation, the above described process for localizing the phrenic nerve, and if the phrenic nerve is so localized, the control device switches to a breathing mode of operation.

Also featured are methods for localizing the phrenic nerve and for establishing negative pressure respiration in a patient who has stopped natural breathing, that are embodied in such an apparatus and devices of the present invention. Such apparatuses, devices and methods of the present invention also are particularly advantageous as they are suitable for use in pulmonary resuscitation of a patient who has stopped natural breathing on their own, such as in the case of traumatic injuries as well as cardiac events. Such apparatuses, devices and methods of the present invention also are advantageous as emergency personnel (e.g., EMTs) can utilize such apparatuses, devices and methods in combination with other emergency techniques such as chest compression and/or cardiac defibrillation.

According to one aspect of the present invention there is featured a portable negative pressure ventilation apparatus that includes a monitoring and sensing device that is operably coupled to a body, for monitoring and sensing a characteristic of the body or bodily function and providing an output signal(s) representative of the sensed characteristic, at least one electrode patch and a control device. In more particular embodiments, the monitoring and sensing device is operably coupled to the body so as to provide an output that is representative of whether or not the body is breathing.

The at least one electrode patch includes a body attachment structure and a multiplicity of electrodes that are mechanically attached to the body attachment structure so as to be in a predetermined orientation. The body attachment is configured and arranged so as to be removably secured to the body. In further embodiments, the at least one electrode patch is disposed on one side of the neck of the body in general proximity to the phrenic nerve. In yet further embodiments, the portable negative pressure ventilation apparatus includes a plurality of such electrode patches, where one patch is located on one side of the neck in general proximity to the phrenic nerve on that side of the neck and a second patch is located on the other side of the neck in general proximity to the phrenic nerve on that side of the neck.

In yet further embodiments, the portable negative pressure ventilation apparatus further includes a ground electrode that is disposed in general proximity to each of the at least one electrode patch or plurality of patches. The ground electrode in combination with the multiplicity of electrodes of each of the at least one electrode patch or the plurality of electrode patches establishes a current pathway between the electrodes being energized and the ground electrode. In more particular embodiments, the ground electrode is located so that the current flows in a downwardly direction (i.e., towards the diaphragm).

In yet further embodiments, each of the multiplicity of electrodes is configured so that a proximal end portion of each electrode forms a needle like structure and has a length sufficient so that the proximal end of the proximal end portion extends through a portion of the skin. In yet further embodiments, the electrode patch is configurable to have N electrodes per patch where N is greater than or equal to 2 and the electrodes can be in any of a number of arrangements including a single line of N electrodes, two spaced lines of N/2 electrodes per line, two spaced lines of electrodes having unequal number of electrodes in the two lines and electrodes in one or more predetermined patterns that is not a straight line (e.g., serpentine). In more particular embodiments, the electrodes are arranged to form P columns of electrodes, where P is greater than or equal to 1 or in yet more particular embodiments, P is greater than or equal to 2.

In yet further embodiments, the body attachment structure includes a layer of a moldable bio-compatible material such as that known to those skilled in the art. The moldable material layer opposes the patient's neck when the body attachment structure is being applied to the neck. The moldable material layer is provided so that it and thus the electrode patch can be molded to the contour of the patient's neck. In more particular embodiments, the body attachment structure comprises a first layer and a second layer. The second layer is composed of a flexible plastic material through which the electrodes 132 can be inserted and the first layer is the moldable material layer.

In yet further embodiments, the body attachment structure comprises a plastic (e.g., plexiglass) outer surface layer and a flexible adhesive inner surface layer. The second layer is removed after the electrodes have been inserted into the skin. The first layer is composed of a flexible bio-compatible material having an adhesive applied to the inner surface that can contour to the patient's neck.

In yet further alternative embodiments, the negative pressure ventilation apparatus includes at least one deep flexible electrode in lieu of, or in addition to, the at least one electrode patch. Such a deep flexible electrode can be used alone or in combination with the ground electrode. Each of the at least one a deep flexible electrode is configured and arranged for insertion into the skin and to stimulate the phrenic nerve when such an electrode is appropriately activated or energized.

Each of the deep flexible electrodes further includes an insertion device, such as a trocar, that is removably disposed within a flexible cannula of the deep flexible electrode. The insertion device is configured and arranged to facilitate insertion of the cannula into the skin and is removed from the cannula after the cannula is disposed within the skin at the desired depth. In this way, the flexible cannula remains disposed within the skin during breathing. The cannula is further configured and arranged so as to include one or more electrodes that are used to stimulate the phrenic nerve. In further embodiments, the one or more deep flexible electrodes are used in combination with the ground electrode as herein described.

The control device is operably coupled to each of the sensing means and the electrodes and is configured and arranged to initially and automatically localize the phrenic nerve with respect to a given set of electrodes that is effective, when appropriately energized, for stimulating the phrenic nerve so as to establish negative pressure induced respiration in the body (i.e., Localization Operating Mode). This determination is based on the output signal(s) from the monitoring and sensing means. In the case where the control device also is coupled to a ground electrode, such localize the phrenic nerve is with respect to a given set of electrodes and the ground electrode.

The following discussion refers to embodiments, that do not embody the use of the ground electrode or the deep flexible electrodes for clarity. However, it shall be understood that the reference to electrodes or set of electrodes in the following discussion shall include a ground electrode as well as the one or more electrodes embodied in the deep flexible electrodes as well as the one or more deep flexible electrodes.

The control device also is further configured and arranged so that the electrodes are energized with a train of pulse signals at a given frequency and having a desired amplitude, for a predetermined period of time. If the electrodes being energized are localized with respect to the phrenic nerve, the diaphragm of the patient or body should contract thereby causing the patient to inhale. After the expiration of this time period, the electrodes are de-energized or deactivated. If the patient did inhale, such de-energization should allow the patient to exhale. The detection of such exhaling for example or conditions associate with exhaling (e.g., presence of $CO_2$) are used for example to determine if negative pressure induced respiration is established in the patient's body.

The control device is further configured and arranged so as to repetitively output stimulation signals via the given set of electrodes and not to output such signals when such a determination is made by the control device, thereby continuously stimulating negative pressure induced respiration in the body (i.e., Breathing Operating Mode). In this way, the user can initially determine a given set of electrodes from the multiplicity of provided electrodes which when continuously and repetitively energized and de-energized will cause breathing by the trauma patient by natural contraction of the diaphragm induced by the stimulation of the phrenic nerve.

In further embodiments, the monitoring and sensing means continues monitoring and sensing of the characteristic of the body or bodily function as the control device is continuously stimulating negative pressure induced respiration in the body and provides output signals to the control device representative of the sensed characteristic. The control device also is further configured and arranged to continuously monitor such output signals from the monitoring and sensing means and to one of control the stimulation signals being outputted so as to modify the negative pressure conditions being induced in the body for stimulation or to provide an indication to the user of a unsatisfactory condition (e.g., not breathing, not enough $CO_2$ in exhale). For example, the control device can alter the frequency of the stimulation signals, the amplitude of the signals and/or the duration of the pulse train of such stimulation signals.

In yet further embodiments, the apparatus further includes an alarm for providing one of an auditory or visual signal to the user. The control device also is further configured and arranged so as to output a signal to activate the alarm when the control device is unable to initially determine the given set of electrodes in the Localization Operating Mode. In this way, the EMT or other medical personnel would be advised that they should start bagging the patient or using any of a number of PPV techniques known to those skilled in the art. The control device also can be further configured and arranged so that the signal to activate the alarm is outputted in the Breathing Operating Mode, to provide the indication of the unsatisfactory condition such as the patient's stoppage of breathing. As the apparatuses of the present invention are intended for use with pulmonary resuscitation, such auditory and visual alarms provide a mechanism by which the emergency personnel can react to the changed conditions while they are performing other life saving techniques (e.g., chest compression).

In yet further embodiments, the control device is further configured and arranged to include a module that initially and automatically determines, in the Localization Operating Mode, the given set of electrodes from the arrangement of the multiplicity of electrodes, said module including means for selectively energizing arrays of given electrodes with stimulation signals and de-energizing such electrodes, for determining from said selective energizing and de-energizing which array(s) of electrode array establish negative pressure induced respiration, where one of the determined arrays is identified as the given set of electrodes.

In yet further and more particular embodiments, the control devices is further configured and arranged to include a module including processing circuitry and a program for execution on the processing circuitry for initially and automatically localize the phrenic nerve with respect to the given set of electrodes. Such a program includes instructions, criteria and code segments for selecting one subset array of electrodes from a predetermined number of subset arrays of the multiplicity of electrodes, energizing the selected subset array of electrodes with stimulation signals, de-energizing such electrodes and evaluating the output signal from the monitoring and sensing means for the selected subset array and determining if the output signal indicates the presence of negative pressure induced respiration in the body.

In the case where said evaluating and determining does not indicate the presence of negative pressure induced respiration, said program further includes selecting another subset array of electrodes from the predetermined number of subset arrays, and repeating said energizing, de-energizing and evaluating. In other words, the described process is repetitively preformed so as to localize the phrenic nerve with respect to the electrode patch and also to determine the particular subset array that is effective for stimulating the phrenic nerve.

In the case where said evaluating and determining does indicate the presence of negative pressure induced respiration, then the program identifies the selected subset array of electrodes or selected another subset array resulting in such an indication as the given set of electrodes, and thereafter repetitively energizes such given electrodes with stimulation signals and thereafter de-energizes such electrodes as herein described so as to thereby continuously stimulate negative pressure induced respiration in the body.

In yet further embodiments, the program further includes instructions, criteria and code segments for requesting the user (e.g., emergency medical personnel, EMT) to input specific patient information. Such an embodiment also includes selecting one or more characteristics of the stimulation signal used for energizing each subset array and the given set of electrodes based on the inputted specific patient information. In yet more particular embodiments, the specific patient information relates to the age and body type of the patient and the module includes a database having a plurality operational characteristics for stimulation signals, the plurality of operational characteristics being related to different age ranges and a body types. Further such selecting includes selecting the stimulation signal operational characteristic(s) whose age range and body type corresponds to the inputted specific patient information.

According to another aspect of the present invention, there is featured a device kit for emergency medical use for inducing respiration in a patient unable to breath on their own. Such emergency medical use includes in the field use such as by EMT's or emergency personnel (e.g., firefighters) responding to an emergency call involving a trauma patient as well as usage in a clinical setting or hospital by medical personnel (e.g., emergency room). Such a device kit includes at least one electrode patch including a body attachment structure and a multiplicity of electrodes that are mechanically attached to the body attachment structure so as to be in a predetermined orientation, the body attachment being configured and arranged so as to be removably secured to the body. In more particular embodiments, such a device kit further includes a plurality of such electrode patches.

Such a device kit also includes a monitoring and sensing means for monitoring and sensing a characteristic of the body or bodily function and providing an output signal(s) representative of the sensed characteristic when it is operably coupled to the body and a control device. In further embodiments, such a device kit also includes an enclosure in which are stored or housed, the electrode patch/patches, ground electrodes and/or deep flexible electrodes, the monitoring and sensing means and the control device. Reference shall be made to the foregoing discussion as to the different types of electrode patches that can be include in such a device kit.

Such a control device is configured as herein described, so as to be operably coupled to each of the sensing means and the electrodes and also to initially and automatically localize the phrenic nerve with respect to a given set of electrodes that is effective, when appropriately energized, for stimulating the phrenic nerve so as to establish negative pressure induced respiration in the body, said determination being based on the output signal(s) from the monitoring and sensing means (i.e., Localization Operating Mode), and repetitively output stimulation signals via the given set of electrodes when such a determination is made by the control device, thereby continuously stimulating negative pressure induced respiration in the body (i.e., Breathing Operating Mode).

The monitoring and sensing means also continues monitoring and sensing of the characteristic of the body or bodily function while the control device continuously stimulates negative pressure induced respiration in the body and provides output signals to the control devices representative of the sensed characteristic. The control device is further configured and arranged to continuously monitor such output signals from the monitoring and sensing means and to one of control the stimulation signals being outputted so as to modify the negative pressure conditions being induced in the body for stimulation or to provide an indication to the user of a unsatisfactory condition.

According to yet another aspect of the present invention there is featured a method for localizing a phrenic nerve located in the neck of a body. Such a method includes the steps of: providing an electrode patch including a multiplicity of electrodes that are in a predetermined orientation; removably securing the electrode patch to the neck so that at least some of the electrodes are in general proximity to the phrenic nerve and monitoring and sensing a characteristic of the body or bodily function and providing an output signal(s) representative of the sensed characteristic. Such a method also includes selecting one subset array of electrodes from a predetermined number of subset arrays of the multiplicity of electrodes, energizing the selected subset array of electrodes with stimulation signals, de-energizing the electrodes, and evaluating the output signal from the monitoring and sensing means for the selected subset array and determining if the output signal indicates the presence of negative pressure induced respiration in the body. In the case where said evaluating and determining does not indicate the presence of negative pressure induced respiration, selecting another subset array of electrodes from the predetermined number of subset arrays, and repeating said energizing, de-energizing and evaluating, and in the case where said evaluating and determining does indicate the presence of negative pressure induced respiration, identifying the selected subset array of electrodes or selected another subset array resulting in such an indication as the given set of electrodes that are localized to the phrenic nerve.

In yet further embodiments, such a method further includes requesting the user to input specific patient information; and said energizing includes selecting one or more operational characteristics of the stimulation signal used for energizing based on the inputted specific patient information. In more particular embodiments, the specific patient information relates to age and body type of the patient; said energizing further includes providing a database having a plurality operational characteristics for stimulation signals, the plurality of operational characteristics being related to different age ranges and a body types; and said selecting includes selecting the stimulation signal operational characteristic(s) whose age range and body type corresponds to the inputted specific patient information.

In yet further embodiments, the provided electrodes are configured so that a proximal end portion of each electrode forms a needle like structure and said localizing includes acting on the provided electrodes so that a proximal end of the proximal end portion extends through a portion of skin of the body and is disposed within the body. In yet further embodiments, the electrode patch is configurable to have N electrodes per patch where N is greater than or equal to 2 and the electrodes can be in any of a number of arrangements including a single line of N electrodes, two spaced lines of N/2 electrodes per line, two spaced lines of electrodes having unequal number of electrodes in the two lines and electrodes in one or more predetermined patterns that is not a straight line (e.g., serpentine). As also described herein, a ground electrode is provided which in combination with the electrodes of the electrode patch are used in connection with the stimulation of the phrenic nerve. Other configurations of electrode patches are described herein. In addition, the provided electrodes can include a ground electrode or one or more deep flexible electrodes as herein described.

According to yet another embodiment of the present invention, there is featured a method for inducing negative pressure respiration in a body using one or both of the phrenic nerves located in the neck of a patient's body. Such a method includes removable securing one or both electrode patches, each patch including a multiplicity of electrodes that are in a predetermined orientation to the neck so that at least some of the electrodes are in general proximity to the phrenic nerve; monitoring and sensing a characteristic of the body or bodily function and providing an output signal(s) representative of the sensed characteristic; and localizing the phrenic nerve with respect to a given set of electrodes that is effective, when appropriately energized, for stimulating the phrenic nerve so as to establish negative pressure induced respiration in the body, said determination being based on the output signal(s) from the monitoring and sensing means. Such a method also includes de-energizing the given set of electrodes for a period of time, after stimulation signals or a pulse train comprising such signals, have been applied for a predetermined time. Such a method also includes repetitively outputting stimulation signals and de-energizing such electrodes via the given set of electrodes when such a determination is made, thereby continuously stimulating negative pressure induced respiration in the body.

In further embodiments, such localizing of the phrenic nerve includes selecting one subset array of electrodes from a predetermined number of subset arrays of the multiplicity of electrodes, energizing the selected subset array of electrodes with stimulation signals, de-energizing such electrodes and evaluating the output signal from the monitoring and sensing means for the selected subset array and determining if the output signal indicates the presence of negative pressure induced respiration in the body. In the case where said evaluating and determining does not indicate the presence of negative pressure induced respiration, such methods includes selecting another subset array of electrodes from the predetermined number of subset arrays, and repeating said energizing, de-energizing and evaluating. In the case where said evaluating and determining does indicate the presence of negative pressure induced respiration, identifying the selected subset array of electrodes or selected another subset array resulting in such an indication as the given set of electrodes that are localized to the phrenic nerve.

In yet further embodiments, such methods further include requesting the user (e.g., EMT) to input specific patient information, the specific patient information relating to at least age and body type of the patient. Such energizing further includes providing a database having a plurality operational characteristics for stimulation signals, the plurality of operational characteristics being related to different age ranges and a body types, and selecting an operational characteristic(s) of a given stimulation signal used for energizing whose related age range and body type corresponds to the inputted specific patient information. Such operational characteristics include pulse amplitude, pulse frequency and/or duration of the pulse train of simulation signals.

In yet further embodiments, in such methods the provided electrodes are configured so that a proximal end portion of each electrode forms a needle like structure and said localizing includes acting on the provided electrodes so that a proximal end of the proximal end portion extends through a portion of skin of the body and is disposed within the body. In yet further embodiments, the electrode patch is configurable to have N electrodes per patch where N is greater than or equal to 2 and the electrodes can be in any of a number of arrangements including a single line of N electrodes, two spaced lines of N/2 electrodes per line, two spaced lines of electrodes having unequal number of electrodes in the two lines and electrodes in one or more predetermined patterns that is not a straight line (e.g., serpentine). As also described herein, a ground electrode is provided which in combination with the electrodes of the electrode patch are used in connection with the stimulation of the phrenic nerve. As also described herein, a ground electrode is provided which in combination with the electrodes of the electrode patch are used in connection with the stimulation of the phrenic nerve. Other configurations of electrode patches are described herein. In addition, the provided electrodes can include a ground electrode or one or more deep flexible electrodes as herein described.

In yet further embodiments, the monitoring and sensing means continues monitoring and sensing of the characteristic of the body or bodily function as stimulating signals are being repetitively outputted resulting in negative pressure induced respiration in the body and provides output signals representative thereof (Breathing Operating Mode); and such methods include continuously monitoring such output signals from the monitoring and sensing means and in response to such output signals to one of (a) control the stimulation signals being outputted so as to modify the negative pressure conditions being induced in the body for stimulation or (b) provide an indication to the user of a unsatisfactory condition. (e.g., not enough $CO_2$ in exhale). For example, the control device can alter the frequency of the stimulation signals, the amplitude of the signals and/or the duration of the pulse train of such stimulation signals.

In yet further embodiments, such methods include providing an alarm that generates one of an auditory or visual signal to the user; and activating the alarm when one of (a) said localizing cannot localize the phrenic nerve with respect to the given set of electrodes or (b) to indicate the presence of an unsatisfactory condition. In this way, the EMT or other medical personnel are advised in either the Localizing Operating Mode or the Breathing Operating Mode that they should initiate pro-active measures such as bagging the patient.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 2B is a pictorial Sagittal view of a neck further illustrating neck anatomy (Moeller, Pocket Atlas of Sectional Anatomy, Vol. I, 2007).

FIG. 3B is block diagram view of a negative ventilation device according to the present invention.

DESCRIPTION OF THE PREFERRED EMBODIMENT

Figure 3A:
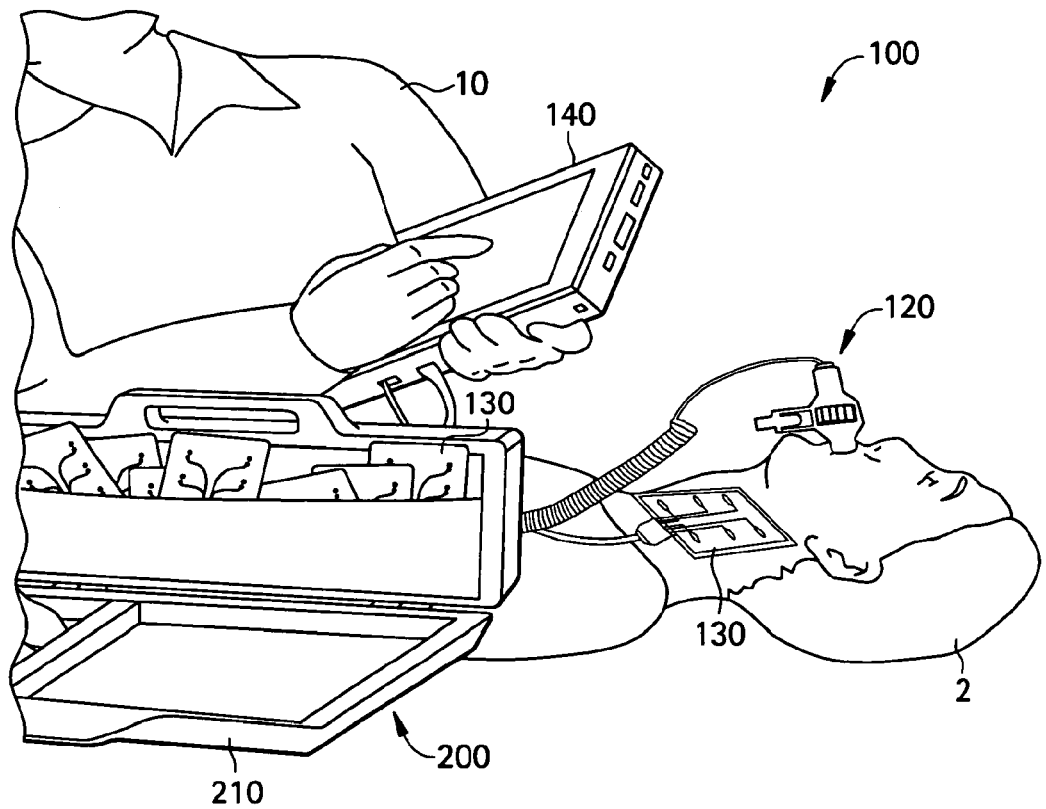
FIG. 3A is a pictorial view illustrating features of a negative ventilation device and device kit according to the present invention and use of such a device.
Figure 4A:
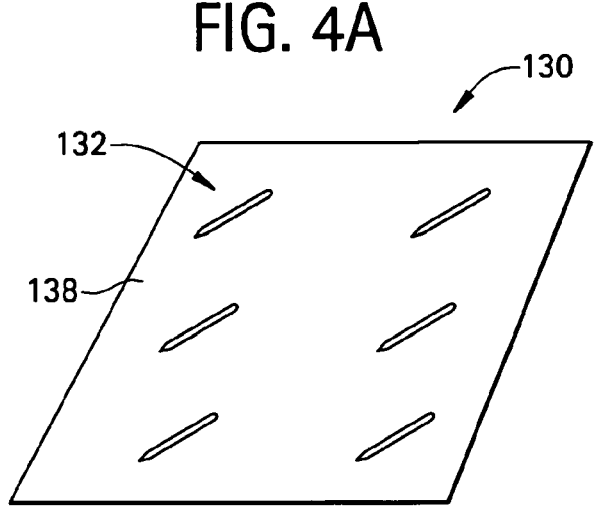
FIG. 4A-C are various views of an electrode patch according to an embodiment of the present invention.
Figure 4B:
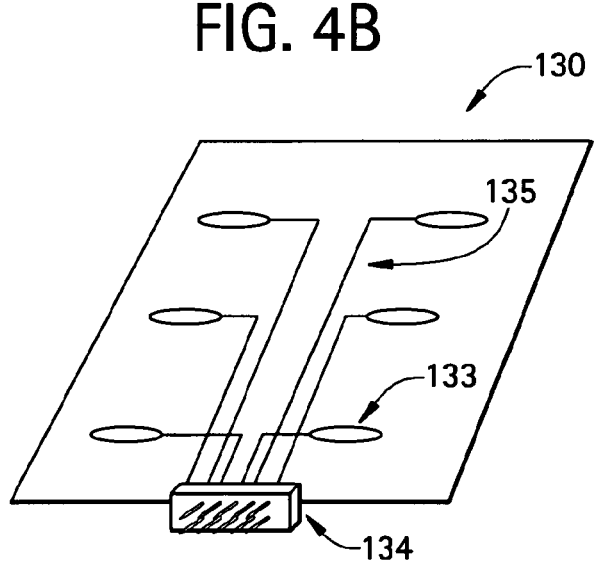
Figure 4C:
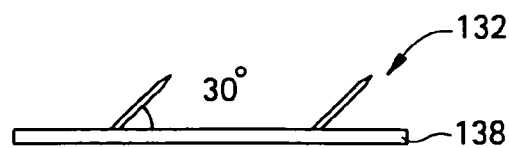
Figure 5:
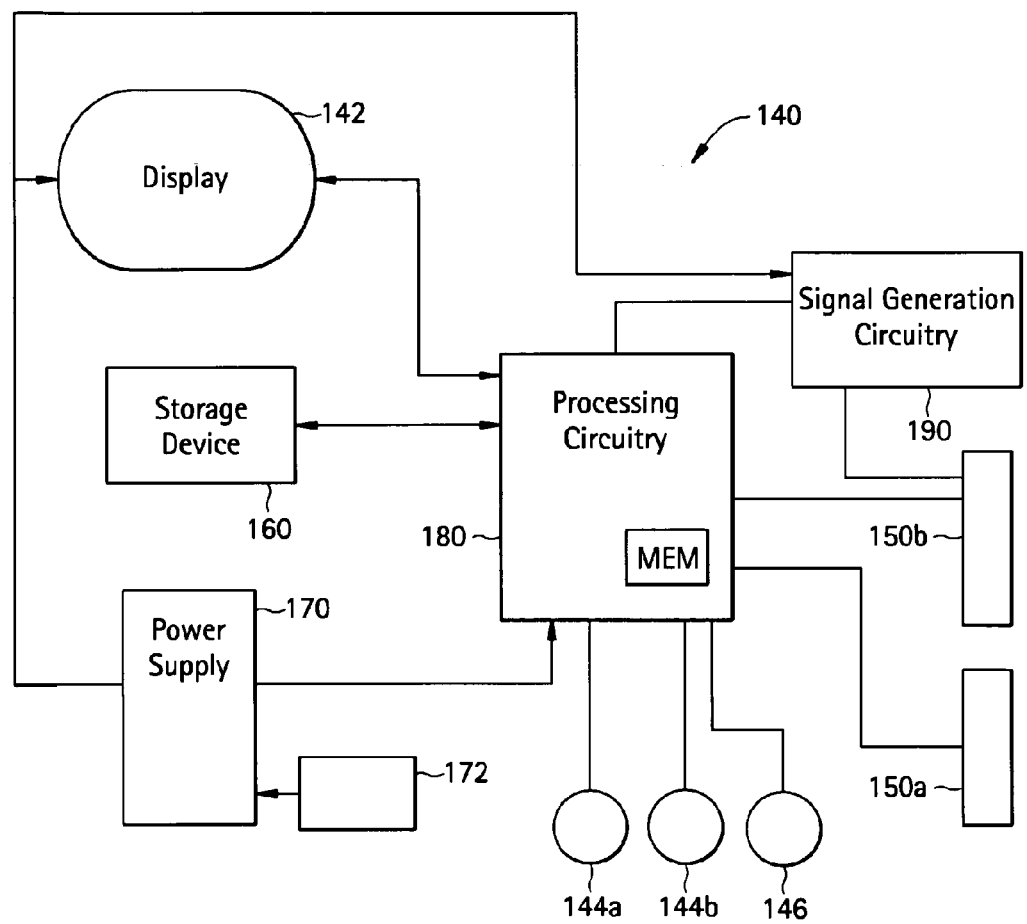
FIG. 5 is a block diagram of a control unit according to the present invention.

Referring now to the various figures of the drawing wherein like reference characters refer to like parts, there is shown in FIG. 3A a pictorial view that illustrates major subunits or components of a negative ventilation device 100 according to the present invention. Also, there is shown in FIG. 3B a block diagram of such a negative ventilation device 100 according to the present invention. Various views of an electrode patch 130 according to an embodiment of the present invention is shown in FIGS. 4A-C and a block diagram of a control unit according to the present invention is shown in FIG. 5. Reference shall be made to these figures in connection with the following discussion.

In FIG. 3A, a user 10 (e.g., clinician, emergency room personnel, hospital personnel, and emergency personnel such as EMT or firefighters) is shown operating the negative ventilation device 100 so as to cause negative pressure ventilation in the patient by electrically stimulating the phrenic nerve at the appropriate frequency so as to thereby to cause the diaphragm to contract. As also shown, the user 10 has operably coupled a monitoring and sensing device 120 and a electrode patch 130 to a patient 2 (e.g., a trauma patient) and to the stimulation unit or control unit 140 of the present invention to effect such operation.

The monitoring and sensing device 120 of such a negative pressure ventilation device 100 is any of a number of mechanisms as is know to those skilled in the art that monitors and provides an output measurement of a bodily characteristic or bodily function that can be used to provide an indication of the breathing by natural contraction of the diaphragm. In more particular embodiments, the monitoring and sensing device 120 is any of a number of mechanisms or devices as is know to those skilled that provide a measurement of air flow or $CO_2$ efflux from the mouth of the patient such as for example, a pneumotachograh flow meter or a $CO_2$ efflux meter. In yet further embodiments, such a device or mechanism is fluidly coupled to the mouth or is coupled to an endotrachial tube when the patient is intubated with such a tube.

The monitoring device also is operably and communicatively coupled to the control unit 140 using cables, wires or the like which allow output signals from the monitoring and sensing device 120 representative of an output measurement of a bodily characteristic or bodily function to be communicated to the control unit for processing. As described herein, such signals are communicated during the process of localizing the phrenic nerve and thereafter when the patient is breathing by natural contraction of the diaphragm due to the stimulation of the phrenic nerve by the device of the present invention. As described hereinafter, the monitoring and sensing device 120 is used by the control unit to determine the electrodes of the patch best suited for stimulating the phrenic nerve while allowing a user to place the electrode patch 130 in the general area of the phrenic nerve and (b) to confirm to the user that the stimulation signals being outputted are still inducing patient breathing.

Figure 1:
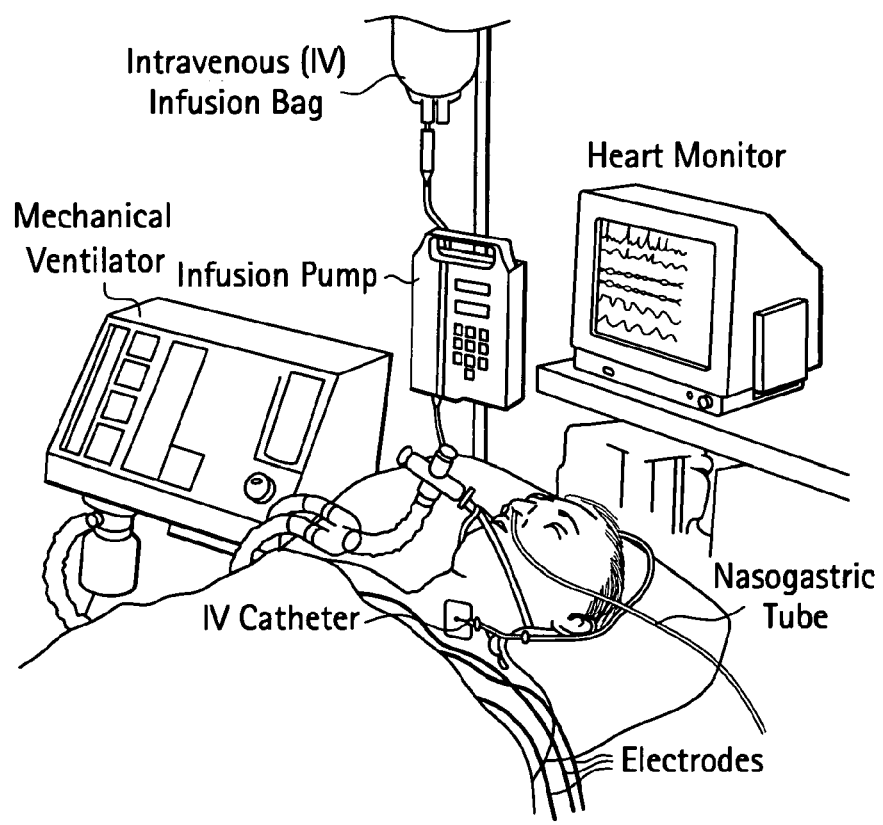
FIG. 1 is a pictorial view illustrating a patient setting in which a mechanical ventilator is being used for ventilation.
Figure 2A:
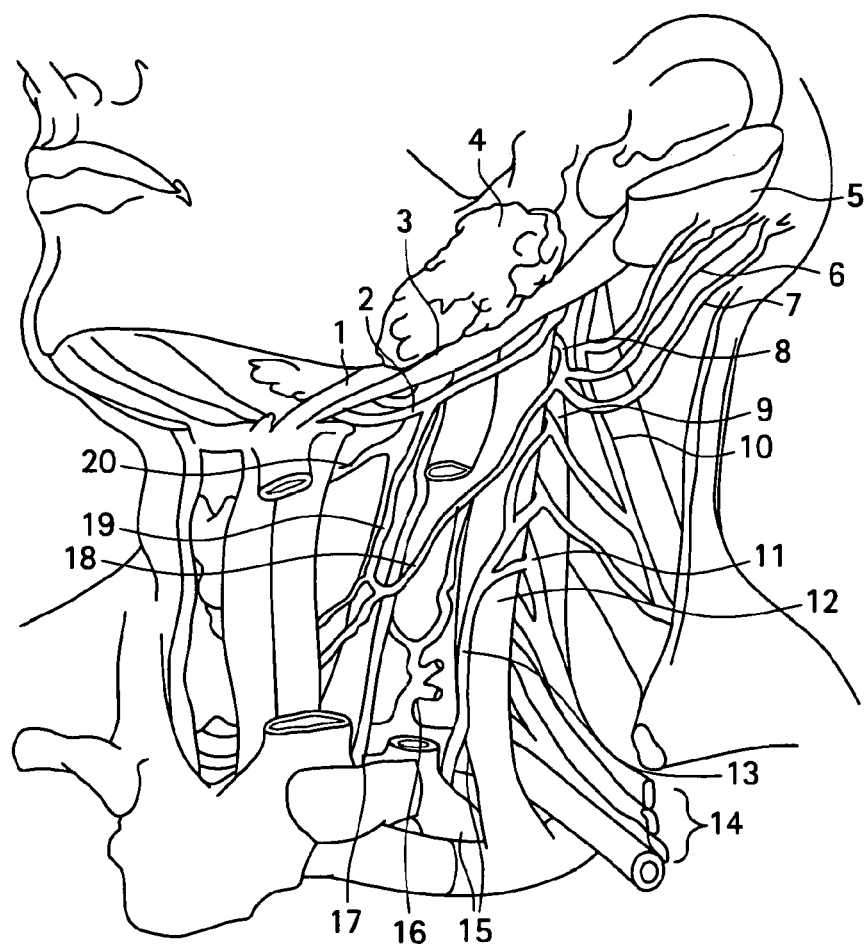
FIG. 2A is a pictorial view of a neck illustrating neck anatomy (Bailey, Head and Neck Surgery; Otoloarynology, 2004).

As shown in FIG. 3A, the electrode patch 130 is located on the neck of the patient and as more particularly discussed herein, the electrode patch is located on the neck at a location which is in general proximity to the phrenic nerve (see FIG. 2A). In this way, the electrical signals that emanate from at least some electrodes of the electrode patch stimulate the phrenic nerve so as to thereby in turn cause the patient to breath by natural contraction of the diaphragm. As described further herein, the control unit 140, monitoring and sensing device 120 and the electrode patch 130 work together to localize the phrenic nerve, or stated another way, work together to determine the particular electrodes of the electrode patch which are best suited to stimulate the phrenic nerve for causing such breathing by natural contraction of the diaphragm. In more specific embodiments, the electrode patch is removably applied to the neck in the region of the posterior border of the sternocleidomastoid muscle at the approximate level of the crecoid cartilage. In yet further embodiments, the electrode patch 130 is disposable.

Each of the electrodes 132 of the electrode patch 130 is operably and communicatively coupled to the control unit 140 using cables, wires or the like which allow stimulation signals to be selectively outputted from each of the electrodes in the processes described herein. More specifically, each electrode 132 is interconnected to a connector 134 or coupling by interconnecting wire 135. The connector 134 in turns is operably and communicatively coupled to the control unit 140 by means of cables wires or the like. In a particular embodiment, the connector 134 is coupled to the control unit 140 by ribbon wire cable 136. As described herein, the stimulation signals or the current pulses comprising such signals is selectively communicated via the cables and connector to the selected electrodes for purposes of stimulating the phrenic nerve.

More particularly, the control unit 140 selectively energizes groups of electrodes for example, each group includes a pair of electrodes, with the stimulation signals in connection with the process to determine the electrodes of the patch best suited for the continued stimulation of the phrenic nerve. It is within the scope of the present invention for the groups of electrodes be arranged so as to include M electrodes, where M is greater than or equal to 2 and so that the M electrodes create any of a number of possible combinations from the multiplicity of electrodes. For example, the group of electrodes can form a two-dimensional array such as an array having two electrodes located that are spaced from a third electrode.

While the negative pressure ventilation device 100 of the present invention as shown in FIG. 3A embodies a single electrode patch 130 applied to one side of the neck it is within the scope of the present invention, for the negative pressure ventilation device 100 of FIG. 3A to be configured so as to embody two or more electrode patches 130 that are each connected to the control unit 140. Reference shall be made to FIGS. 3A, B and the foregoing discussion for details not shown in FIG. 3C.

Figure 3C:
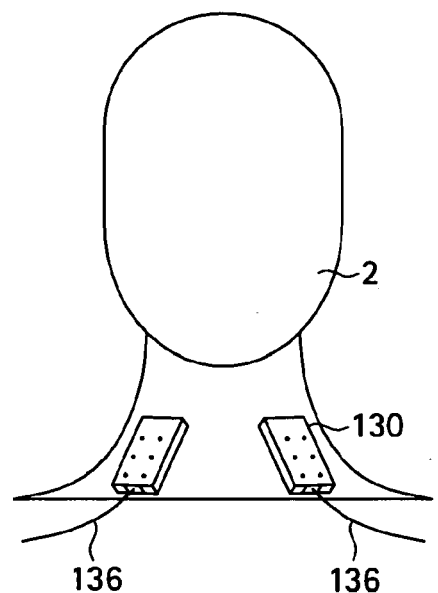
FIG. 3C is an illustrative view showing another aspect of the present invention in which the negative ventilation device of FIGS. 3A-B, embodies two electrode patches.

As shown in FIG. 3C, the two electrode patches 130 are located on both sides of the neck. These two electrode patches are located so that one patch is located on one side of the neck in general proximity to the phrenic nerve on that side of the neck and a second patch is located on the other side of the neck in general proximity to the phrenic nerve on that side of the neck.

Depending upon the patient's physical condition and status, stimulating one phrenic nerve may be sufficient to provide adequate ventilation for a given patient. However, despite the added complexity associated with the addition or one or more electrode patches, it may be desirous to provide two electrode patches to stimulate both phrenic nerves in the neck so as to more completely stimulate the diaphragm. For example, while stimulating one phrenic nerve may induce negative pressure breathing in a patient such breathing may prove less than ideally effective (e.g., $CO_2$ in exhalation may be considered less than ideal). While it is possible to modify the characteristics of the stimulation signals to compensate for this, the addition of the second electrode patch and stimulation of the second phrenic nerve also is considered to effect improved breathing characteristics.

When the negative pressure ventilation device 100 embodies one or more electrode patches 130, at least one of the electrodes 132 of the electrode patch is connected so it functions as a ground electrode, i.e., connected to the negative terminal of the signal generation circuitry 190 (FIG. 5) and one or more of the remaining electrodes of the patch are connected to the positive terminal so that the current corresponding to each signal pulse of the stimulation signal(s) flows between the electrodes connected to the positive and negative terminals.

Figure 3D:
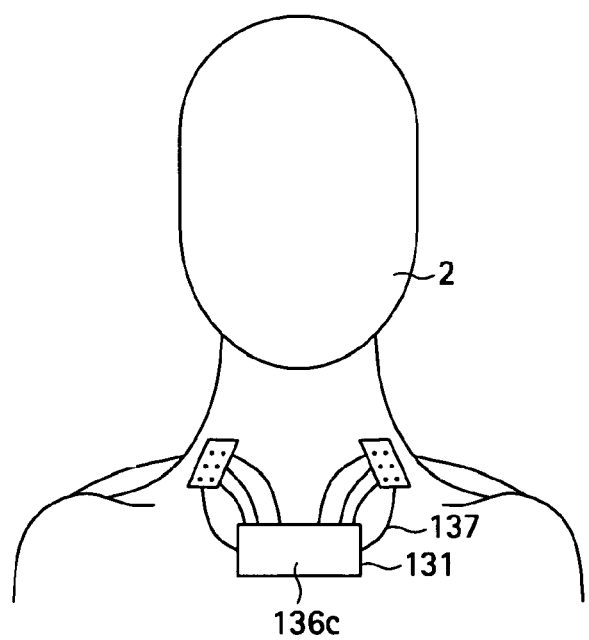
FIG. 3D is an illustrative view showing yet another aspect of the present invention in which the negative ventilation device of FIGS. 3A-B embodies two electrode patches and a ground electrode.

In further embodiments, the negative pressure ventilation device 100 of FIG. 3A also is configurable so as to embody a separate ground electrode 131 that is used in combination with one electrode patch 130 or with two or more electrode patches such as illustrated in FIG. 3D. Reference shall be made to FIGS. 3A-C and the foregoing discussion for details not shown in FIG. 3D.

The ground electrode in combination with the multiplicity of electrodes of each of the at least one electrode patch or the plurality of electrode patches establishes a current pathway between the electrodes being energized and the ground electrode. In more particular embodiments, the ground electrode is located so that the current flows in a downwardly direction (i.e., towards the diaphragm).

In such an arrangement, the ground electrode 131 is spaced from the electrode patches 130 and thus the electrodes 132 so as to increase the depth and length of the current path 137. In more particular embodiments, the ground electrode 131 is located at, or proximal, the sternum, particularly, when the negative pressure ventilation device embodies two electrode patches. The ground electrode 131 and each of the electrode patches 130 are connected to the control unit 140 so that the stimulation signals selectively pass between selected groups of electrodes of the multiplicity of electrodes electrode and the ground electrode. In such a case, one or more of the electrodes of each electrode patch 130 are connected to the positive terminal so that the current corresponding to each signal pulse of the stimulation signal(s) flows between from the electrodes of the electrode patch to the ground electrode. It should be noted that it is within the scope of the present invention for one or more of the electrodes of the electrode patch to also be operably coupled to the negative terminal.

Figure 3E:
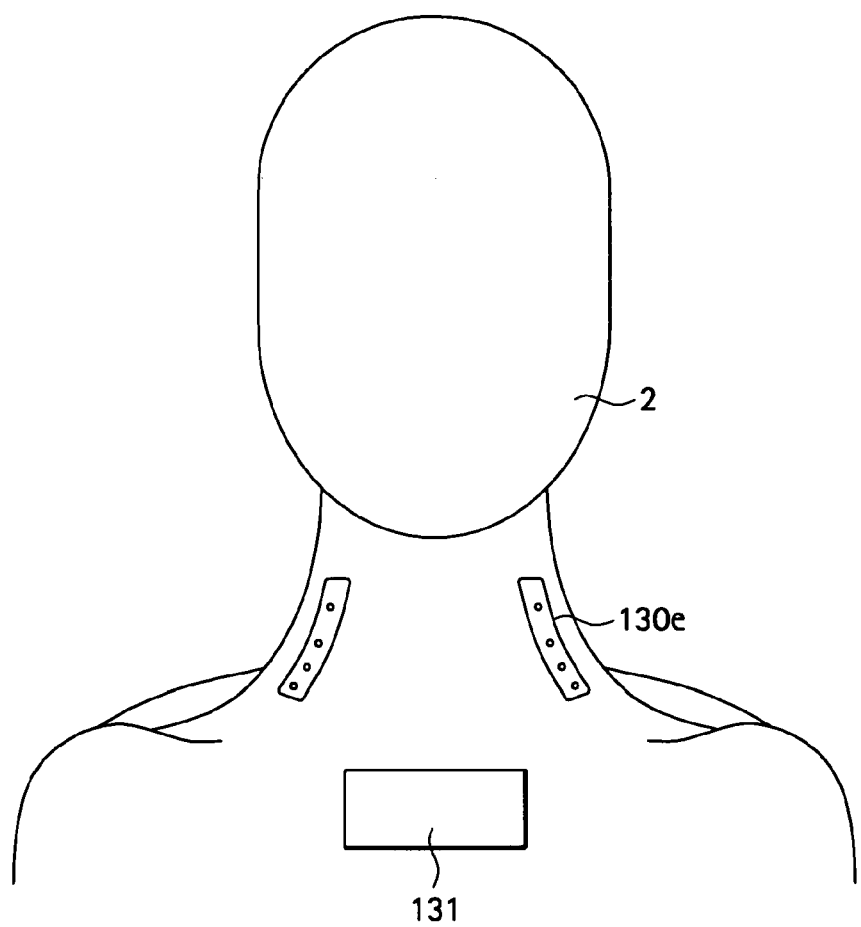
FIG. 3E is an illustrative view showing yet another aspect of the present invention in which the negative ventilation device of FIGS. 3A-B, embodies two strip type electrode patches and a ground electrode.

In the above described embodiments, the electrodes 132 of the electrode patch 130, and as described in more detail herein, are generally configured so that the electrodes form one or more columns of electrodes. This is not limiting. Referring now to FIGS. 3E and 4H, there is shown yet another embodiment in which the negative pressure ventilation device 100 of FIG. 3A is configurable so as to embody one or more strip electrode patches 13e. Such a negative pressure ventilation device 100 also is configurable to further include a ground electrode 131. Reference shall be made to FIGS. 3A-C and the foregoing discussion for details not shown in FIGS. 3E and 4H.

In the illustrated arrangement the electrodes 132 are arranged on a so as to form a single column of electrodes on a base member 138e. The electrodes 132 and the base member 138e generally form a strip like electrode patch whose width is significantly narrower than its length. Such an electrode patch 132 is advantageous in that the surface area of the skin being covered by the electrode patch and the number of electrodes being inserted into the skin is reduced as compared to the other embodiments of the present invention. As indicated above, the one or more strip electrode patches 130e can be used in combination with a separate ground electrode so as to increase the depth and length of the current path. Reference shall be made to the foregoing discussion regarding coupling of electrodes to the negative and positive terminals of the single generation circuitry.

In yet further embodiments, the electrode patch 130 is configurable so that it can take any of a number of forms. There is shown in FIGS. 4A-C one illustrative form of such an electrode patch, a percutaneous electrode patch. This minimally invasive patch is particularly suitable for use with patients that are at risk for traumatic brain injury. Such an electrode patch 130 includes a multiplicity of electrodes that array arranged in a predetermined pattern and mounted on a base member 138 that is made of a semi-rigid bio-compatible material such as plexiglass or nylon.

In an illustrative exemplary embodiment, the electrode patch 130 includes six needle electrodes 132 that are arranged so as to form two columns of three electrodes, where the columns are spaced from each other (e.g., 2 cm spacing) and the electrodes in each column are spaced from each other (e.g., 2 cm spacing). The spacing and electrode arrangement is illustrative, as it is within the skill of those knowledgeable in the arts so as to present the electrodes in a different array arrangement as well as different spacing.

Each needle has a length sufficient such that when the patch 130 is secured to the neck, a proximal end portion of the needle is inserted into the patient's skin a sufficient distance thereby lowering the skin's impedance and thus reducing voltage requirements for the stimulation signal. In an exemplary illustrative embodiment, each electrode has a shank length of 13 mm and is a 30 gauge needle. The needle preferably is of a diameter having sufficient mechanical strength to withstanding operating conditions that can occur in the field but also such as to minimize discomfort when inserting the needle electrode into the skin and while it remains disposed within the skin.

The front of the electrode patch 130, more particularly the base member 138, is coated with a bio-compatible adhesive that removably secures the electrode patch to the skin of the patient. Once the electrode patch 130 is adhered to the patient's skin, each needle electrode 132 is inserted through a marking on the patch and into the patient's skin at an angle (e.g., 15 or 39 degrees to the horizontal). Once inserted, each needle electrode 132 is secured to the patch with an electrode attachment 133 (e.g., butterfly tape) so as to thereby prevent the needle electrodes 132 from dislodging in the movement and vibrations endemic to an in field, emergency situation such as in an ambulance.

In an alternative embodiment, the electrode patch can be configured and arranged as a transcutaneous electrode patch. Such an electrode patch includes N circular electrodes that are each coated with a conductive gel, where N is an integer greater than 2. In particular illustrative embodiments, there are six electrodes that are each 1 cm in diameter and spaced 2 cm apart from each other. As with the electrode patch 130 described above, the front of the patch is coated with adhesive for removably securing the patch to the patient's skin.

Figure 8:
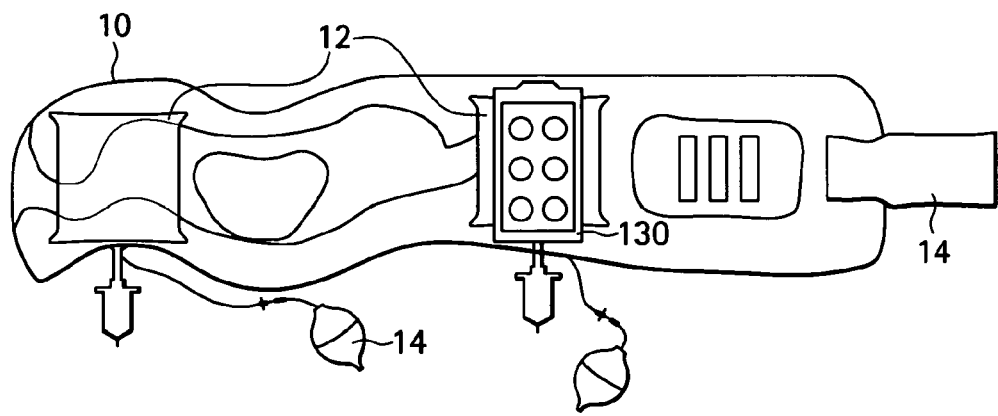
FIG. 8 is a pictorial view illustrating use of an electrode patch in combination with a neck brace.

In further embodiments, and to ensure firm contact of the transcutaneous electrodes with the skin and to minimize the distance between the electrodes and the phrenic nerve, an ordinary cervical collar 20 such as shown in FIG. 8, is augmented with an inflatable cushion 22. The inflatable cushions 22 are adhered to the cervical collar in the positions shown in FIG. 8. Additionally, the cushion has a pressure sensor and pumping mechanism 26 to aid the user in inflating the cushion to the right size. Such a cervical collar 20 also typically includes a Velcro type securing means 24 for securing the collar about the neck.

Figure 4D:
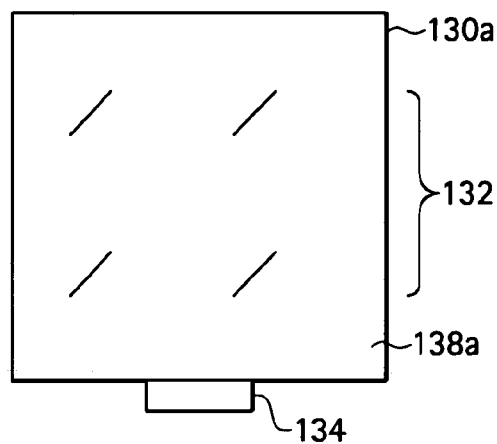
FIG. 4D is an illustrative view of an electrode patch according to another embodiment of the present invention.

Referring now to FIG. 4D there is shown an electrode patch 130a according to another embodiment of the present invention. The electrode patch 130a of this embodiment is arranged so as to include a base member 138a on which is disposed two columns of electrodes 132, each column including two electrodes (i.e., four total electrodes). As described herein, the electrodes are connected to a connector 134 and the connector 134 is in turn operably coupled to the control unit 140.

Figure 4E:
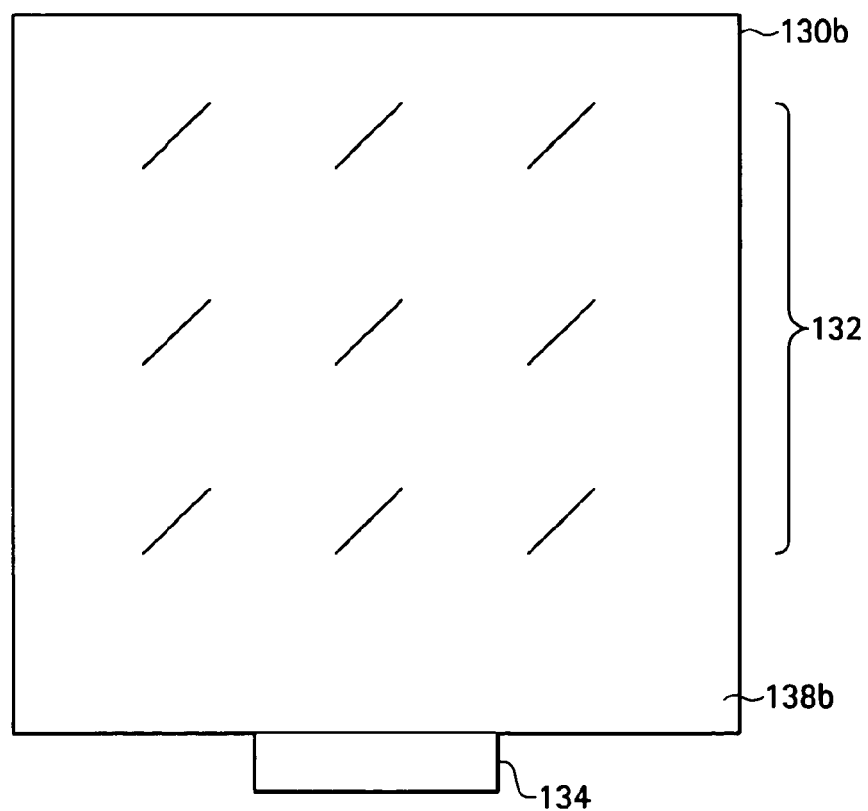
FIG. 4E is an illustrative view of an electrode patch according to yet another embodiment of the present invention.

Referring now to FIG. 4E there is shown an electrode patch 130b according to yet another embodiment of the present invention. The electrode patch 130b of this embodiment is arranged so as to include a base member 138b on which is disposed three columns of electrodes 132, each column including three electrodes (i.e., nine total electrodes). As described herein, the electrodes are connected to a connector 134 and the connector 134 is in turn operably coupled to the control unit 140.

Figure 4F:
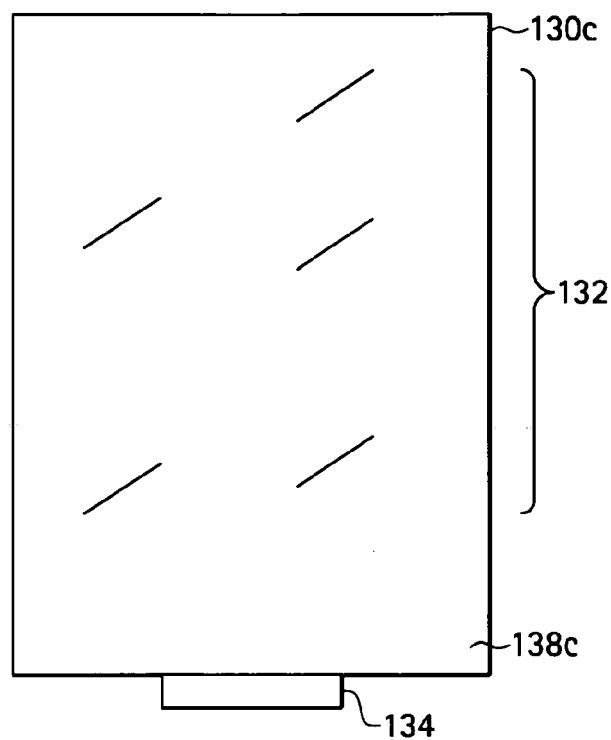
FIG. 4F is an illustrative view of an electrode patch according to yet another embodiment of the present invention.

Referring now to FIG. 4F there is shown an electrode patch 130c according to yet another embodiment of the present invention. The electrode patch 130c of this embodiment is arranged so as to include a base member 138c on which is disposed two columns of electrodes 132, one column including three electrodes and the second column including two electrodes (i.e., five total electrodes). As described herein, the electrodes are connected to a connector 134 and the connector 134 is in turn operably coupled to the control unit 140.

Figure 4G:
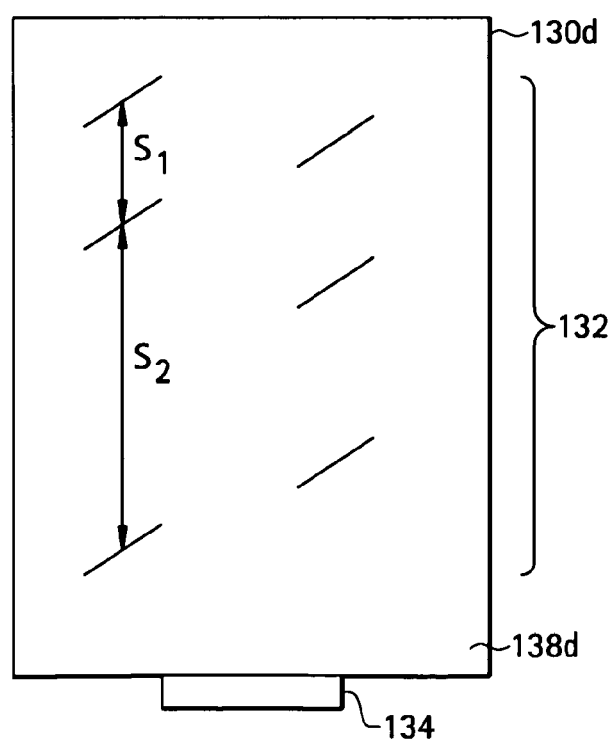
FIG. 4G is an illustrative view of an electrode patch according to yet another embodiment of the present invention.
Figure 4H:
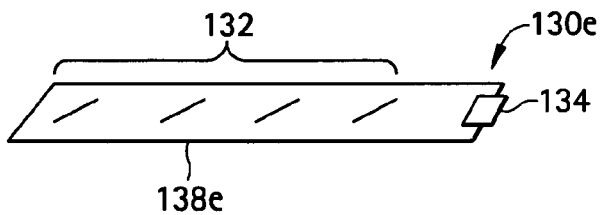
FIG. 4H is an illustrative view of the strip electrode patch of FIG. 3E.

Referring now to FIG. 4G there is shown an electrode patch 130d according to yet another embodiment of the present invention. The electrode patch 130d of this embodiment is arranged so as to include a base member 138d on which is disposed two columns of electrodes 132, each column including three electrodes (i.e., six total electrodes). In this embodiment, the electrodes in one column are not equal spaced from each other. Rather two electrodes are spaced from each other by a distance S1 and two electrodes are spaced from each other by a distance S2 (one of them being in common with the first two electrodes) are spaced from each other by a distance S2. where S1 does not equal S2. As described herein, the electrodes are connected to a connector 134 and the connector 134 is in turn operably coupled to the control unit 140.

Figure 4I:
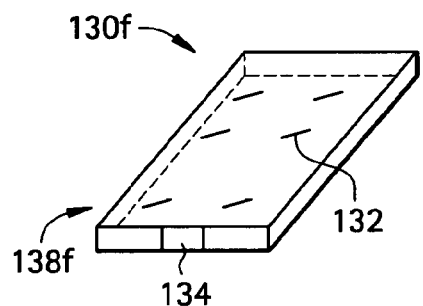
FIG. 4I is an illustrative view of an electrode patch according to yet another embodiment of the present invention and FIG. J is a side view thereof.
Figure 4J:
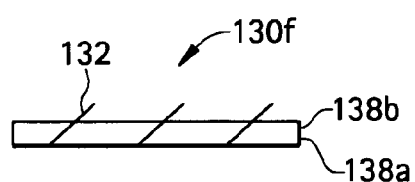
FIGS. 4K-L are illustrative views of an electrode patch according to yet another embodiment of the present invention.
FIG. 4M is an illustrative view of a flexible electrode mounted on a removable trocar usable with the negative ventilation device according to yet another aspect of the present invention.
FIG. 4N is an illustrative view of a flexible electrode when disposed within the tissue of a patient (not shown) with the trocar removed.

Referring now to FIGS. 4I, J there is shown an electrode patch 130f according to yet another embodiment of the present invention. The electrode patch 130f of this embodiment is arranged so as to include a base member 138f on which is disposed two columns of electrodes 132, each column including three electrodes (i.e., six total electrodes). As described herein, the electrodes are connected to a connector 134 and the connector 134 is in turn operably coupled to the control unit 140.

In this embodiment, the base member is composed of a first layer 138a and a second layer 138b. The second layer 138b is composed of a flexible plastic material through which the electrodes 132 can be inserted as hereinafter described. The first layer 138a is composed of a moldable bio-compatible material that can be molded to the contour of the patient's neck.

Figure 4K:
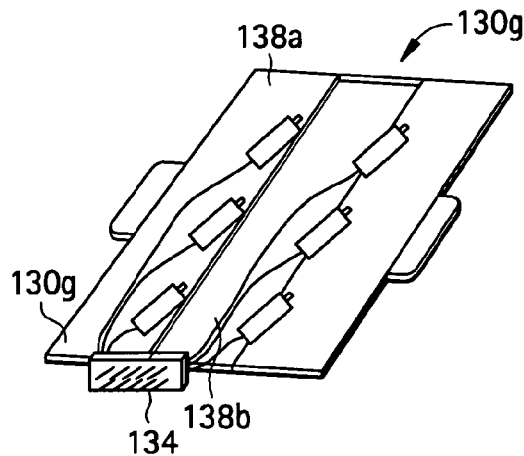
Figure 4L:
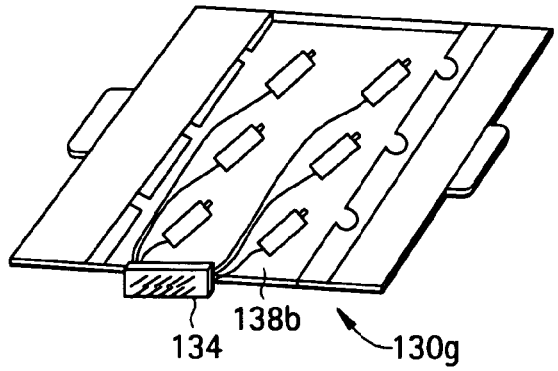

Referring now to FIGS. 4K, L there is shown an electrode patch 130g according to yet another embodiment of the present invention. The electrode patch 130g of this embodiment is arranged so as to include a base member 138g on which is disposed two columns of electrodes 132, each column including three electrodes (i.e., six total electrodes). As described herein, the electrodes are connected to a connector 134 and the connector 134 is in turn operably coupled to the control unit 140.

In this embodiment, the base member is composed of a first layer 138a and a second layer 138b. The second layer 138b is composed of a Plexiglas material that is removed after the electrodes 132 have been inserted into the skin as hereinafter described. The first layer 138a is composed of a flexible bio-compatible material having an adhesive applied to the inner surface that can contour to the patient's neck.

In yet further embodiments, any of the above-described electrode patches of the present invention are configurable to include N electrodes per patch, where N is greater than or equal to 2. Also, the electrodes can form any of a number of arrangements including a single line of N electrodes, two spaced lines of N/2 electrodes per line, two spaced lines of electrodes having unequal number of electrodes in the two lines and electrodes in one or more predetermined patterns that is not a straight line (e.g., serpentine). In more particular embodiments, the electrodes are arranged to form P columns of electrodes, where P is greater than or equal to 1 or in yet more particular embodiments, P is greater than or equal to 2.

Figure 4M:
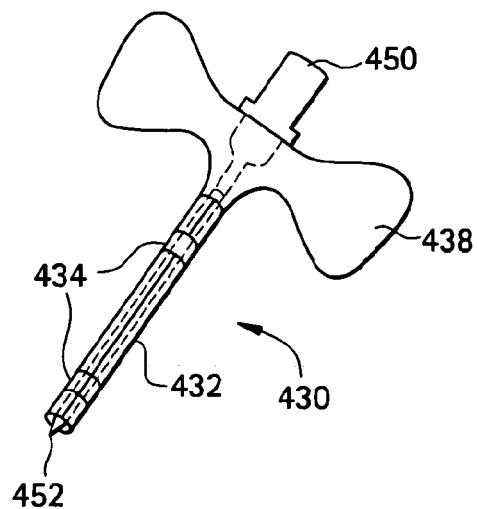
Figure 4N:
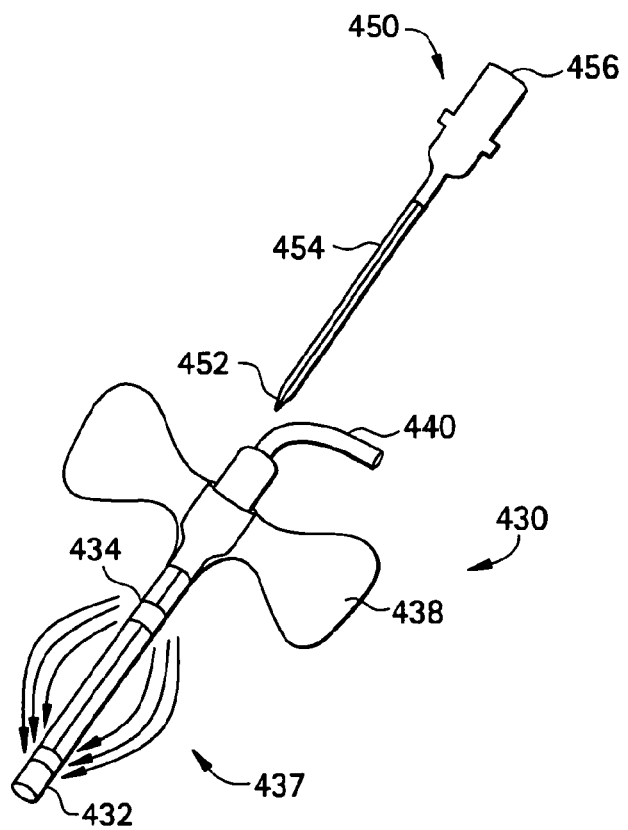

Referring now to FIGS. 4M, N there is shown an flexible deep electrode 430 to according to yet another embodiment of the present invention. In this embodiment, one or more of such flexible deep electrodes 430 are inserted into the skin much like the insertion of the electrodes of an electrode patch of the present invention generally proximal one or both of the phrenic nerves. Such a flexible deep electrode 430 includes a flexible cannula 432 on which are located two or more electrodes or electrode bands 434 and a hub member 438 having lateral extending portions including an adhesive for removably securing the hub member to the patient's skin/body.

As the flexible deep electrode 430 of this embodiment is intended to have a length sufficient that it can be inserted into the skin to a greater depth, a removable trocar 450 is inserted through the hub member 438 so an axially extending portion 454 thereof extends through and along the length of the flexible cannula 432 and so that an end 432 of the axially extending portion extends outwardly from an end of the cannula. Such an end 432 is preferably configured and arranged so as to facilitate penetration of the outer dermal layers. After the flexible cannula 432 is inserted into the skin to a desired depth, the user removes the removable trocar 450 by for example, grasping an end portion 456 thereof. The end portion 456 also is configurable so as to form a stop which rests against the hub member 438 when the end 432 is extending from the cannula end.

When the negative pressure ventilation device 100 of FIG. 3A is configured so as to embody one or more of such deep flexible electrodes 430 in lieu of the electrodes of the electrode patches, the electrode bands 434 are connected to a connector 440 which connector is operably coupled to the control unit 140 including the signal generation circuitry 190 thereof, much the same way as pairs of electrodes of an electrode patch 130 are connected to the control unit. More particularly, one of the bands 434 of the deep flexible electrode 430 is connected so as to function as a ground electrode, i.e., connected to the negative terminal of the signal generation circuitry 190 (FIG. 5) and the other band 434 is connected to the positive terminal so that the current corresponding to each signal pulse of the stimulation signal(s) flows in a path 437 between the electrodes connected to the positive and negative terminals (i.e., the path 437 can be composed of one or more conductive pathways). In yet further embodiments, the negative pressure ventilation device 100 of FIG. 3A is configured so as to embody a plurality of such deep flexible electrodes 430, where one or more of the plurality of deep flexible electrodes are utilized to stimulate the phrenic nerve.

In yet further embodiments, the negative pressure ventilation device 100 of FIG. 3A is configurable so as to embody a separate ground electrode 131 in combination with the one or more deep flexible electrodes. The ground electrode in combination with the electrode bands 434 each of the one or more deep flexible electrodes establishes a current pathway between the electrode bands being energized and the ground electrode. In more particular embodiments, the ground electrode is located so that the current flows in a downwardly direction (i.e., towards the diaphragm).

Referring now back to FIG. 3B, the control unit 140 combines the output from the monitoring and sensing device 120 and as described further herein includes hardware and software to generate the signal to energize electrodes of the electrode patch 120 or the electrode bands of the deep flexible electrodes to localize and stimulate the phrenic nerve. In general the control unit controls overall operation of the negative pressure ventilation device 100 including controlling the processes associated with determining the electrodes or groups of electrodes best suited for stimulating the phrenic nerve, stimulating the phrenic nerve to achieve the natural contraction of the diaphragm and providing warnings to the user 10 when certain conditions are found to exist.

The control unit 140 can be in the form of a touch screen computer where the user touches the screen to input data, instructions and operating parameters or it can be in the form of a stand alone unit having input control buttons or a control panel in combination with a display.

As shown in FIGS. 3B and 5, the control unit 140 includes a display 142 that can be in the form of a touch screen of a touch screen computer a visual alarm 144a (e.g., an LED) and an auditory alarm 144b (e.g., speaker). In alternative embodiments, the control unit 140 is arranged so that the visual alarm is embodied in the display 142. Such visual and auditory alarms 144 *a,b* are well known to those skilled in the art and thus are not discussed further herein. The visual and auditory alarms 144 *a,b* are operably coupled to the processing circuitry (e.g., microprocessor, ASIC) so that when a determination is made that one or both of the alarms 144 *a,b* need to be activated, the control unit outputs a signal(s) to activate the alarm(s).

In further embodiments, the speaker comprising the auditory alarm 144b also is adapted to deliver verbal or auditory messages or queues to a user 10 in connection with use of the negative ventilation device 100. In more particular embodiments, the verbal or auditory messages are stored in the storage device 160 (e.g., conventional laptop hard, flash hard drive or flash memory) of the control unit 140. When the processing circuitry 180 determines that certain conditions exist for delivery of a verbal or auditory message or queue, such a verbal message is retrieved from the storage device 160 by the processing circuitry and the processing circuitry causes the auditory alarm speaker to output the retrieved verbal message.

While operation of the control unit 140 is generally carried out by using the touch screen or display 142, the control unit also is further configurable so as to include a manually operated on/off switch 146 that turns the control unit 140 and the functionalities thereof on or off responsive to actuation of the switch by a user. As the control unit 140 is preferably configured and arranged so as to be portable and for use in the field, such a device includes a power supply 170 as is known to those skilled in the art and appropriate for the intended use and operational conditions. For example, the power supply can be any one of a number of re-charge batteries known those in the art (e.g., nickel metal hydride, Li ion or the like).

Thus, the control unit 140 is further configurable so as to include a port or connector 172 that is coupled to the battery or power supply 170 and which can be coupled to a external power source (e.g., electrical wall outlet) using any of a number of techniques known to those skilled in the art. The processing circuitry 180 also can be configured and arranged to monitor the power status of the power supply 170 and provide appropriate indications on the touch screen/display 142 and/or by providing visual or auditory alarms 144 *a,b* when the power supply needs to be re-charged.

Such a control unit also includes connectors 150*a,b* that are appropriate for operably coupling the wiring 122, 136 coming from the monitoring and sensing device 120 and the electrode patch 130 to the processing circuitry. Similarly, connectors are provided so as to operably coupled the ground electrode 131 and each of the one or more deep flexible electrodes 430 to the control unit 140. Such connectors 150*a,b* are well known to those skilled in the art and thus need not be detailed further herein.

The control unit 140 also signal generation circuitry 190 that is operably coupled to the processing circuitry and the connector 150b which is operably coupled to the electrode patch 130. The signal generation circuitry 190 is configured and arranged so as to generate the stimulation signals having a desired strength and frequency so as to stimulate the phrenic nerve responsive to control signals from the processing circuitry. Such signal generation circuitry 190 also is operably coupled to the power supply 170 for purposes of generating the signals. Such signal generation circuitry 190 also is configured and arranged so as to step up the voltage supplied by the power supply 170 so that a signal having a desired voltage and current is outputted by the signal generation circuitry 190. As also described herein such signal generation circuitry and processing circuitry also is configured and arranged so outputting of signals to the electrodes is stopped so as to allow the patient to exhale.

Figure 6:
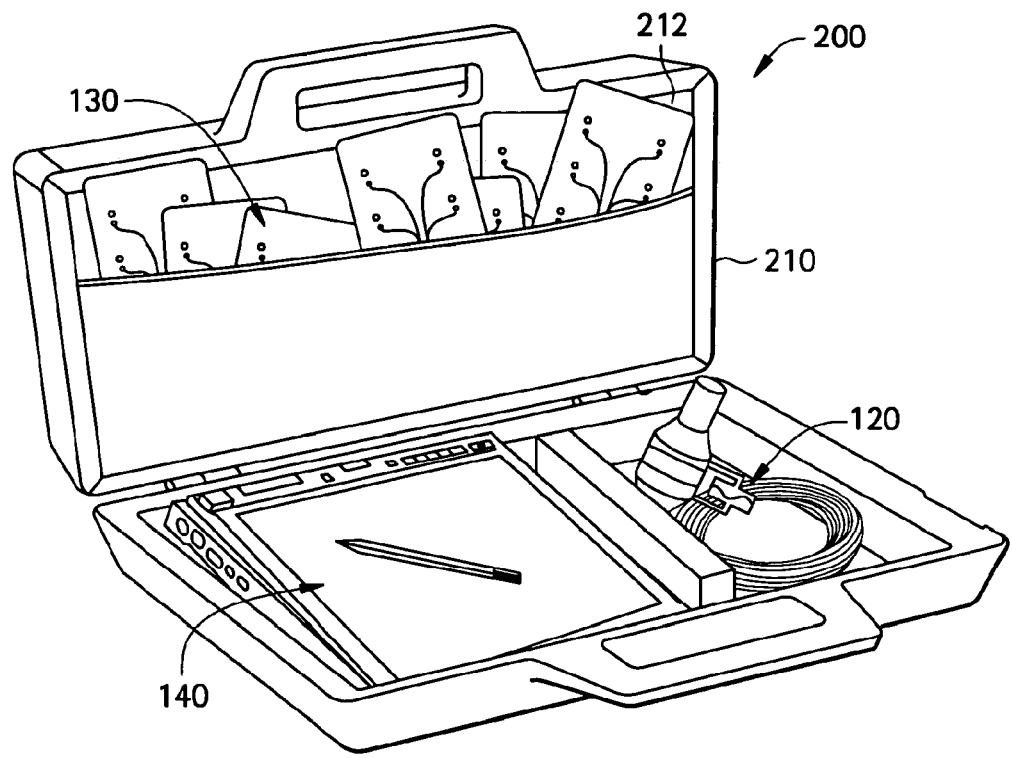
FIG. 6 is a pictorial view of an illustrative embodiment of a device kit according to the present invention.

In an illustrative embodiment and with reference also to FIG. 6, when the monitoring and sensing device 120, the electrode patch 130, the ground electrode 131 and/or deep flexible electrodes 430 and the control unit 140 are not in use, they can be stored inside the device kit enclosure 210 thereby forming a device kit 200. As the electrode patch 130, ground electrode 131 or deep flexible electrode 430 are disposable, the device kit enclosure 210 further includes a compartment 212 in which can be stored a plurality, more specifically a multiplicity of electrode patches, ground electrodes and/or deep flexible electrodes.

The housing 210 can be any of a number of structures known to those skilled in the art for storing and transporting the monitoring and sensing device 120, the electrode patch 130, ground electrode and/or deep flexible electrodes 430 and the control unit 140 from a storage location to a location in the field or within a hospital where a use is contemplated or needed. In more particular embodiments, the enclosure 210 is in the forms of a plastic case having interior dimensions and compartmenting sufficient for housing and protecting the monitoring and sensing device 120, the electrode patches 130, ground electrodes and/or deep flexible electrodes 430 and the control unit 140 as they are being stored therein.

Figure 7A:
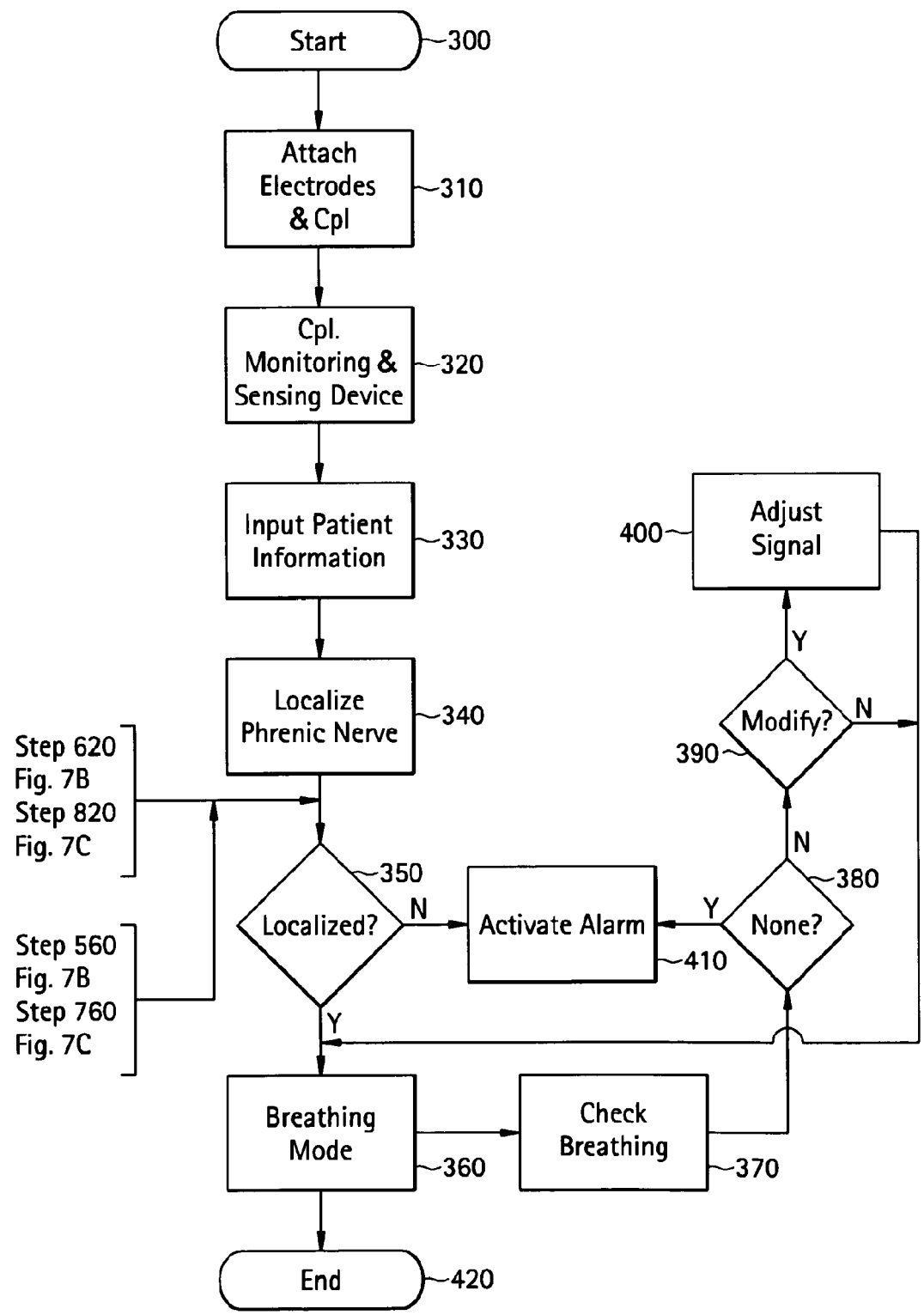
FIGS. 7A-C are high level flow diagrams illustrating an operational methodology embodied in the negative ventilation device (FIG. 7A), one methodology embodied in the negative ventilation device for localizing the phrenic nerve (FIG. 7B) and another methodology embodied in the negative ventilation device for localizing the phrenic nerve using two electrode patches (FIG. 7C).
Figure 7B:
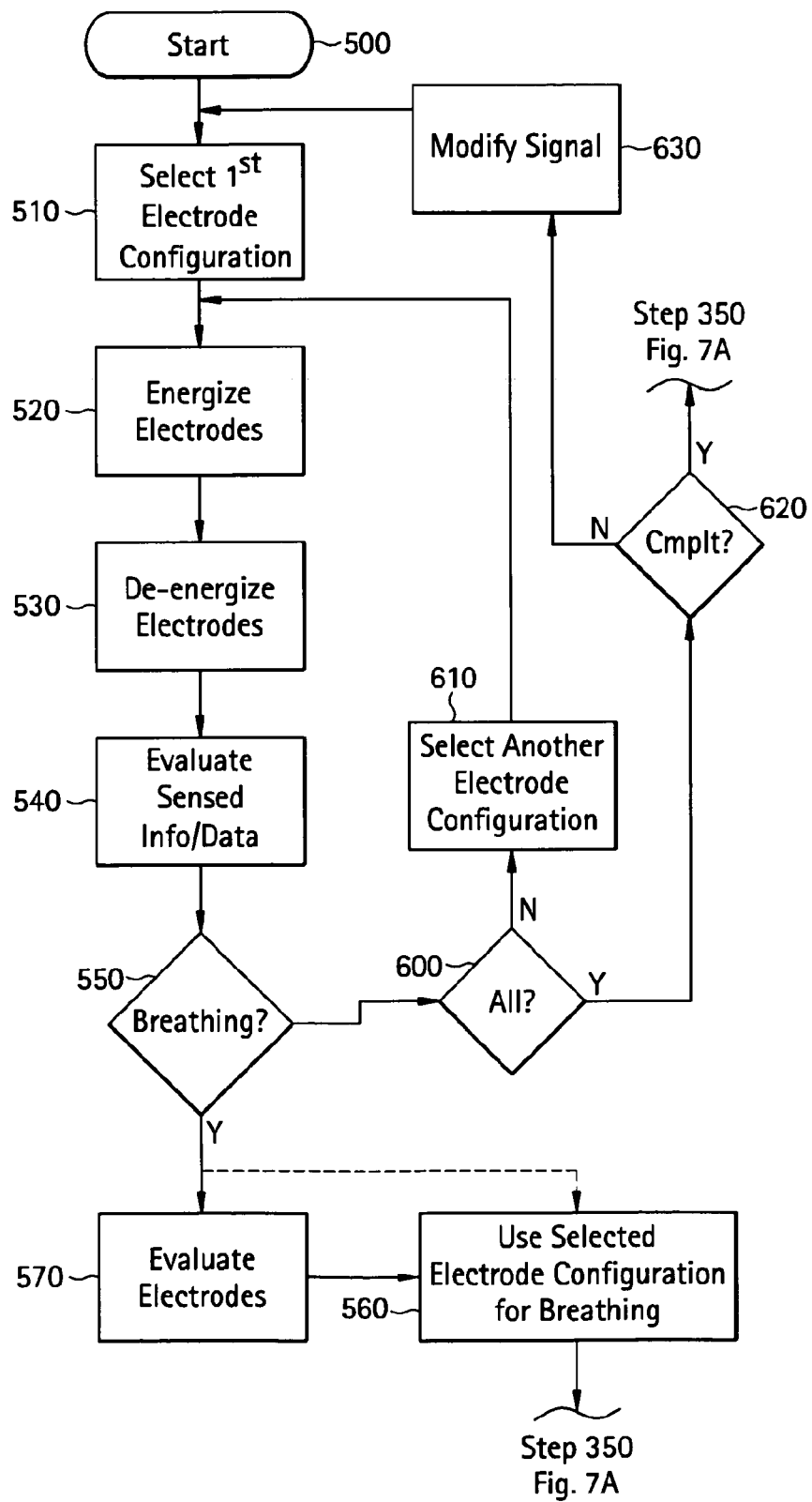
Figure 7C:
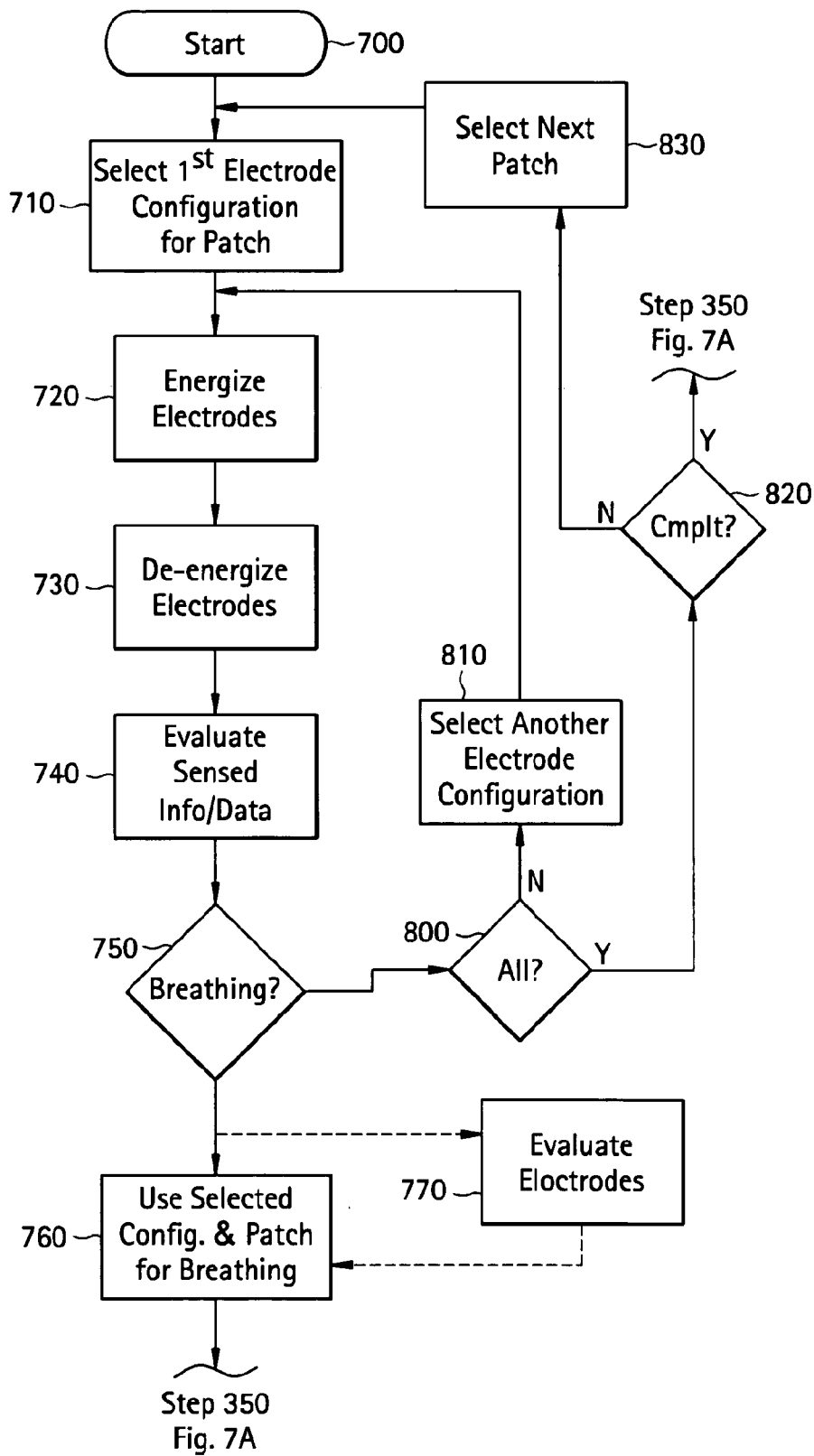

The operation of the control unit 140 and thus also the negative pressure ventilation device 100 of the present invention can be best understood from the following discussion and with reference to the flow diagrams shown in FIGS. 7A-C. Reference also should be made to FIGS. 3-6 and 8 for further details and features not otherwise shown in FIGS. 7A-C. It should be recognized that it is within the skill of those knowledgeable of the software programming arts to write program code, code segments to carry out the instructions embodied in the control unit as are set forth in FIGS. 7A-C in combination with the following discussion.

When emergency personnel are in a situation where a patient 2 is not breathing, requires pulmonary resuscitation, requires CPR or otherwise is in a condition in which patient breathing needs to be induced or augmented, the user 120 starts (Step 300) the process associated with use of the negative ventilation device 100 of the present invention. In such a case, the user would open up the device kit 200 and extract the subunits of the device 100. As indicated herein, Such apparatuses, devices and methods of the present invention are advantageous as emergency personnel (e.g., EMTs) can utilize such apparatuses, devices and methods in combination with other emergency techniques such as chest compression and/or cardiac defibrillation.

The user would then locate the electrode patch 130 or the plurality of such electrode patches on the neck as herein described so that each patch is removably, adhesively secured to the skin of the neck at a location in proximity to one or both of the phrenic nerves and also operably couple each patch to the control unit 140 via the appropriate connector 150*a*, Step 310. This would include inserting each of electrode needles 132 into the skin and securing the deployed needles in such a way that they do not come lose during usage.

In the case where deep flexible electrodes 430 were being used, the user would insert one or more of the deep flexible electrodes into the skin at a location that is in proximity to one or both of the phrenic nerves in the neck. The user also would operably couple each of the one or more deep flexible electrodes to the control unit via the appropriate connector(s) 150*a*. As indicated herein, this would include inserting each electrode 430 to a desired depth in the skin and securing the deployed electrode in such a way that they do not come lose during usage.

In the case where the ventilation device 100 is configured to include a separate ground electrode 131, the user would operably couple the ground electrode to the patient's body in a location appropriate for stimulating the phrenic nerve and the diaphragm in conjunction with applying each electrode patch to the neck or inserting the deep flexible electrodes. The user also would operably couple the ground electrode 131 to the control unit via an appropriate connector, for example another connector 150*b*.

In addition, the user would appropriately and operably couple the monitoring and sensing device 120 to the patient 2 (e.g., fluidly couple to the mouth or a intubation tube) so the device monitors and senses a characteristic of the body or bodily function and also operably couples the monitoring and sending device to the control unit 140, Step 320.

After so configuring the electrode patch(es) 130, ground electrode 131, and/or the deep flexible electrodes 430, the monitoring and sensing device 120 and the control unit 140, the user would turn on the control unit so as to initialize the control unit and thus, also the negative pressure ventilation device 100, Step 340. It should be recognized that such initializing of the control unit 140 can be done at any time before attempting to localize the phrenic nerve and thus steps 310, 320 and 340 can be done in any order. In an exemplary illustrative embodiment the control unit 140 is in the form of a touch screen computer having a Linux operating system, were the computer and software is configured to boot immediately into the software written for the device for carrying out the processes described herein. Thus, the user 10 need not go through the usual process for causing a program to become activate.

In particular embodiments, a panel is displayed to the user by the display 142 with basic options, for inputting patient specific information such as settings for the relative size and age of the patient. This first "basic panel" is a user-friendly abstraction of more detailed parameter configuration such as the amount of current (in mA) the device 100 supplies to the patient 2 via the electrode patch 130, ground electrode, and/or deep flexible electrodes. In more particular embodiments, the user 10 sets the size and age of the patient 2 to one of five options: infant, child, adult, large adult, very large adult. This will in turn automatically set the magnitude of the current to a value between 5 and 50 mA.

In further embodiments, after inputting such information, the panel displays additional information such as recommendations or instructions for the number of electrode patches 140 to use or the use of deep flexible electrodes 430 based on the inputted information. For example, the number of electrode patches can be specified to match weight and age of the patient.

In alternative embodiments, the user 10 can configure these parameters directly as well as view the stimulation signal waveform and the waveforms from the monitoring and sensing. For example, the basic panel is configurable with a button marked "More Detail" so that the user can click this button so as to thereby launch this feature. Given the limited time available in emergency situations, it is likely that the user 10 would confine themselves to inputting the minimal patient information necessary to allow the process to continue.

After initializing the control unit 140, the control unit is operated so as to localize the phrenic nerve in the neck (i.e., Localization Operating Mode), Step 340. The process for localizing the phrenic nerve is discussed below in connection with FIG. 7B when the negative pressure ventilation device 100 embodies one electrode patch or FIG. 7C when the negative pressure ventilation device 100 embodies two electrode patches. If this process results in the phrenic nerve being localized to each electrode patch 130 (Yes, Step 350), then the control unit 140 will switch to the Breathing Operating Mode, in which the control unit continues to periodically output stimulation signals to the subset array of electrodes that were active when the breath was detected so as to establish breathing by natural contraction of the diaphragm, Step 360. For example, the control unit would output a train of signal pulses having a frequency and amplitude for a predetermined time period to stimulate the phrenic nerve and thus the diaphragm to cause the patient to inhale and thereafter stop outputting such stimulation signals for a predetermined time period to allow the patient to exhale. For example, this energization and de-energization of the electrodes is provided every six seconds so that the patient is breathing at about 10 bpm.

While the control unit 140 is in the Breathing Mode, the signals from the monitoring and sensing device 120 are continuously monitored to check on the breathing status, Step 370 to determine if the patient is or is not breathing, Step 380. If the patient is not breathing (No, Step 380), one or both of the alarms 144 *a,b* are activated, Step 410. As indicated above, in such a case, the user 10 is to use another breathing technique, such as for example, using a breathing bag to ventilate the patient. If the patient is breathing (Yes, Step 380), then the control unit 140 remains in the breathing mode, Step 360.

In further embodiments, if the patient is still breathing (Yes, Step 380), the control unit evaluates the signals or stream of signals from the monitoring and sensing device 120 to determine if the stimulation signal should be modified, Step 390. If the patient stimulation signal need not be adjusted or modified, (No, Step 380), then the control unit 140 remains in the breathing mode, Step 360.

If the patient stimulation signal need should be adjusted, (Yes, Step 380), then the control unit 140 determines the adjusted parameters for the stimulation signal (e.g., alters frequency, amplitude and/or duration of the stimulation signals), and thereafter the adjusted stimulation signal is continuously outputted to the patient in the breathing mode, Step 360. In alternative embodiment, the control unit 140 can cause an alarm to be generated if the evaluation of the signals or stream of signals from the monitoring and sensing device indicates the presence of an unsatisfactory condition.

The control unit continues to operate in the breathing mode, Step 360, until some action is taken by the user 10 to end this breathing process, Step 420, unless earlier terminated because the patient 2 has stopped breathing despite the outputted stimulation signals.

Referring now to FIG. 7B, there is shown an exemplary process for localizing the phrenic nerve when the ventilation device 100 is configured so as to embody one electrode patch 130. In more particular embodiments, a start button is displayed on the display 142 and the user starts the localization process or "Localization Operating Mode" by pressing the start button, Step 500. The negative pressure ventilation device 100, more particularly the control unit starts the localization process/mode by selecting a first subset of the electrodes 132 or electrode configuration of the electrode patch, step 510. For purposes of discussion, and in an exemplary embodiment, two of the six electrodes are initially selected.

The selected subset array of electrodes is energized or activated, Step 520 or in other words, a stimulation signal(s) is outputted by the selected subset array of electrodes for a predetermined period of time for purposes of stimulating the phrenic nerve so as to cause natural contraction of the diaphragm. In alternative embodiments, there is stimulation circuitry associated with each subset of electrodes, thus such selecting and energizing is accomplished by activating the stimulation circuitry for the intended subset array of electrodes. Such outputting includes generating a train of pulse being generated at a particular frequency appropriate for stimulation of the phrenic nerve and having desired current amplitude based on the inputted patient specific information for a given duration of time. If this first electrode configuration is correct, such stimulation should cause the patient to inhale.

After expiration of the predetermined period of time, signal outputting is stopped so that the configuration of electrodes 132 become de-energized or deactivated, Step 530. Assuming that the patient inhaled as a result of stimulation, such de-energizing of the electrodes allows the patient to exhale, thus completing a natural breathing cycle.

As these stimulations signals are being outputted and the electrodes are being de-energized, the signals or data from the monitoring and sensing device 120 are evaluated to determine if these signals indicate that the patient 2 is breathing, Steps 540, 550. For example, in the case where the monitoring and sensing device 120 embodies a pneumotachograh flow meter, breathing is considered detected by the pneumotachograph signal when the signal inputted is above a small threshold voltage.

If breathing is detected (Yes, Step 550), then the control unit 140 will use the selected electrode configuration for breathing, Step 560 and switch to the Breathing Operating Mode (Step 360, FIG. 7A). Basically, the process returns a yes to the Localizing step (step 350, FIG. 7A so that process proceeds to Step 360.

If breathing is not detected when the subset array of electrodes are being activated (No, Step 550), then the control unit 140 proceeds to determine if all of the possible subset arrays of electrodes or electrode configurations have been activated or cycled, Step 600. If the control unit 140 has not cycled through all of the possible subset arrays of electrodes or electrode configurations (No, Step 600), then the control unit selects another subset array of electrodes or electrode configuration, Step 610 and Steps 520, 530, 540, 550 and 600 are repeated.

If the control unit 140 has cycled through all of the possible subset arrays of electrodes or electrode configurations (No, Step 600), then the control unit 140 then determines if this process has been repeated for N times, Step 620. In such a case, N an integer that is greater than or equal to 1 and in more particular embodiments N is greater than or equal to 2. If the control unit 140 has not cycled through all of the possible subset arrays of electrodes or electrode configurations for N times (No, Step 600), then the control unit remains in the Localization Mode, again selects the first subset array of electrodes or first electrode configuration Step 510, and Steps 520, 530, 540, 550 and 600 are repeated. In this way, the control unit flips through different subset arrays of electrodes (e.g., different pairs of the six electrodes) until a breath is detected or until the control unit 140 has cycled through all of the possible subset arrays of electrodes for N times (Yes, Step 600).

In further embodiments, an evaluation is made to determine if the operating characteristics or parameters of the stimulation signal should be modified such as described above for Step 400 of FIG. 7A. If it is determined that the stimulation signal should be modified, the signal parameters are adjusted and then the process proceeds to step 510 and Steps 520, 530, 540, 550 and 600 are repeated.

If after N cycles no breath is detected, one or both of the alarms 144 *a,b* are activated, Step 410. Basically, the process returns a No to the Localizing Step (Step 350, FIG. 7A) so that the process proceeds to Step 410. In such a case, the user is to use another breathing technique, such as for example, a breathing bag. It should be recognized that the user may click a stop button at any time to halt program execution and any stimulation.

Referring now to FIG. 7C, there is shown an exemplary process for localizing the phrenic nerve when the ventilation device 100 is configured so as to embody two electrode patches 130. In more particular embodiments, a start button is displayed on the display 142 and the user starts the localization process or "Localization Operating Mode" by pressing the start button, Step 700. The negative pressure ventilation device 100, more particularly the control unit starts the localization process/mode by selecting a first subset of the electrodes 132 or electrode configuration of the first electrode patch, step 710. Reference also should be made to the discussion regarding FIG. 7B for details of common features not set forth below.

The selected subset array of electrodes or electrode configuration is energized or activated, Step 720 for a predetermined period of time for purposes of stimulating the phrenic nerve so as to cause natural contraction of the diaphragm. After expiration of the predetermined period of time, signal outputting is stopped so that the configuration of electrodes 132 become de-energized or deactivated, Step 730. Assuming that the patient inhaled as a result of stimulation, such de-energizing of the electrodes allows the patient to exhale, thus completing a natural breathing cycle.

As these stimulations signals are being outputted and the electrodes are being de-energized, the signals or data from the monitoring and sensing device 120 are evaluated to determine if these signals indicate that the patient 2 is breathing, Steps 740, 750. If breathing is detected (Yes, Step 750), then the control unit 140 will use the selected electrode configuration of the first electrode patch for breathing, Step 760 and switch to the Breathing Operating Mode (Step 360, FIG. 7A). Basically, the process returns a yes to the Localizing Step (Step 350, FIG. 7A) so that process proceeds to Step 360. In the case, where both electrode patches are to be used for breathing, then the process proceeds to step 830 and the process repeats for the second electrode patch on the other side of the neck.

If breathing is not detected when the subset array of electrodes or electrode configuration is being activated/de-energized (No, Step 750), then the control unit 140 proceeds to determine if all of the possible subset arrays of electrodes or electrode configurations have been activated or cycled, Step 800. If the control unit 140 has not cycled through all of the possible subset arrays of electrodes or electrode configurations (No, Step 800), then the control unit selects another subset array of electrodes or electrode configuration, Step 810 and Steps 720, 730, 740, 750 and 800 are repeated.

If the control unit 140 has cycled through all of the possible subset arrays of electrodes or electrode configurations (No, Step 800), then the control unit 140 then determines if this process has been repeated for N times, Step 820. In such a case, N is an integer that is greater than or equal to 1 and in more particular embodiments N is greater than or equal to 2.

If the control unit 140 has not cycled through all of the possible subset arrays of electrodes or electrode configurations for N times (No, Step 820), and one of the two electrode patches to is be used for breathing or in the case where both patches are being used for breathing, then the control unit remains in the Localization Mode, again selects the first subset array of electrodes or first electrode configuration for the second patch Step 710, and Steps 720, 730, 740, 750 and 800 are repeated for the second patch.

If after N cycles no breath is detected, one or both of the alarms 144 a,b are activated, Step 410. Basically, the process returns a No to the Localizing Step (Step 350, FIG. 7A), so that the process proceeds to Step 410. In such a case, the user is to use another breathing technique, such as for example, a breathing bag. It should be recognized that the user may click a stop button at any time to halt program execution and any stimulation.

In yet further embodiments, the above described processes of either FIGS. 7B,C are repeated for all possible electrode configurations and each configuration in which breathing was detected is identified. Thereafter, an evaluation is made of each of the breathing and other physiological attributes for these successful electrode configurations to determine the electrode configuration best suited for simulating the phrenic nerve, Step 560, 770. In such a case, the control unit 140 will use the electrode configuration(s) resulting from such an evaluation as the electrodes to be used for the Breathing Operating Mode, Step 560,760.

The foregoing methodology and devices of the present invention are particularly suited for use with standard EMT protocol including intubating the patient 2 with an endotrachial tube. The methodology and devices of the present invention advantageously allows the EMT to place the electrode patch 130 in the general area of the phrenic nerve and thereafter the negative ventilation device 100 can switch between different subset arrays of electrodes (e.g., switch between pairs of electrodes) until a working combination is found. The device 100, more specifically, the control unit 140 thereof, uses the signal from the monitoring and sensing device 120 to determine which subset array of electrodes constitute a working combination, that is, which electrodes of a given subset array, when activated, cause the patient to breathe. Another advantageous effect, is that by having the control unit 140 continuously monitor the signals from the monitoring and sensing device 120 while the patient is breathing using the negative ventilation device 100, provides a feedback mechanism to confirm to the EMTs that the negative pressure ventilation is occurring or warn them that the patient is not breathing. Such continual monitoring of such signal also advantageously provides a mechanism by which the control unit 140 can react to changing conditions and alter or modify the stimulation signal so that patient breathing can be maintained using the device 100.

Referring now to FIGS. 9A-E, an experiment was undertake to assess the viability of the methodology and devices of the present invention using a pig(s). In general the experiment(s) were conducted to determine the efficacy of the preliminary prototype in achieving long-term negative pressure ventilation in a large animal model, to vary stimulation parameters in order to achieve natural breathing and minimize fatigue of the diaphragm muscle fibers during long term negative pressure ventilation (at least more than 30 min), to vary stimulation parameters in order to achieve natural breathing and minimize muscle co-contractions in the neck region and to vary stimulation parameters in order to control ventilation and expired $CO_2$ pressure ($PCO_2$).

Methods:

A female pig was deeply anaesthetized in order to suppress spontaneous breathing and ventilated using a positive pressure mechanical ventilator (PPMV). Needle electrodes were applied proximal to the phrenic nerve at the neck region. Because of the thickness of the pig's skin and the difficulty in localizing the phrenic nerves in a pig, an incision (see FIG. 9D) was made in the pig's skin so that the phrenic nerve could be located and so that needle electrodes could be located in the pigs but remote and not in contact with the phrenic nerve.

As the pig was removed from PPMV, 8-10 mA of current was applied to stimulate the phrenic nerve. A $CO_2$ monitor was used to continuously measure expired $CO_2$ pressure. Various current waveforms and stimulation frequencies were tested in order to achieve natural, sustained breathing and to minimize fatigue of the diaphragm muscle fibers.

Results:

We were able to achieve sustained negative pressure ventilation in the pig for more than two hours while spontaneous breathing of the pig was suppressed. We were able to control the $PCO_2$ at a given level by changing the breaths per minute and/or the duration of each breath. The changes were observed instantaneously on the $CO_2$ monitor. We did not observe any diaphragm or phrenic nerve fatigue for up to two hours during the experiment (because of resource limitations the pig was not ventilated for a longer duration). We did not observe any co-contractions from the neck or shoulder muscles near the phrenic nerve. The pig maintained normal heart rate and blood pressure throughout this experiment with negligible vagal stimulation. We were able to control the breaths per minute, as well as the duration of each breath using our stimulation system.

Figure 9A:
FIGS. 9A-C are pictorial views of an experimental setup involving a pig.
Figure 9B:
Figure 9C:
Figure 9D:
FIG. 9D is pictorial views illustrating an incision in the pig and insertion of a pair of electrodes for stimulating a phrenic nerve.
Figure 9E:
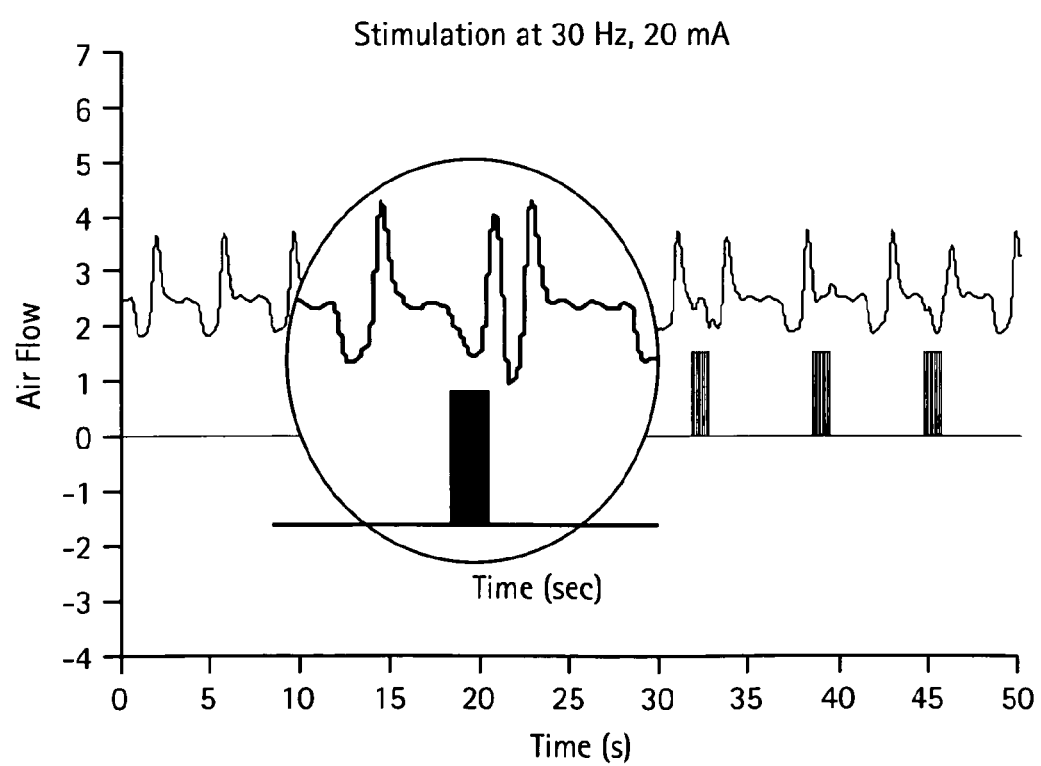
FIG. 9E is a graphical view of airflow for a pig versus time as the pig is being stimulated with signal pulses having a frequency of 30 Hz and a current amplitude of 20 mA.

As shown in FIG. 9E, sustained respiration between instantaneous breaths was observed using a stimulation signal or pulse signal at 30 Hz, 20 mA and having 500 us pulse width. Muscle fatigue was observed at high breathing rates >60 breaths/min.

CONCLUSION/DISCUSSION

In sum, the experiment demonstrated that the preliminary prototype was able to achieve negative pressure ventilation in a large animal model over a period of hours, without causing muscle co-contractions or diaphragmatic fatigue. It also was shown that the device can be used to control tidal volume, respiratory rate and the level of ventilation.

From our previous experiments we have gathered sufficient data to optimize the stimulation waveform required for ventilation. However the swine model was insufficient to test the patient interface and phrenic nerve localization system of our system. The phrenic nerve is located deep below the skin in pigs and its location is extremely variable on both sides and between animals. This makes it impossible to stimulate the nerve using a surface electrode patch in a swine model. We have also conducted dissections to locate the phrenic nerve in canines and they have also proven to be poor models in terms of neck anatomy.

Although a preferred embodiment of the invention has been described using specific terms, such description is for illustrative purposes only, and it is to be understood that changes and variations may be made without departing from the spirit or scope of the following claims.

For example, the negative ventilation device, systems and methods of the present invention can be adapted for use in chronic hospital ventilation as opposed to just in-field use. Also, such devices, systems and methods of the present invention can be adapted or augmented with ultrasound guided needle placement to minimize muscular co-contraction. Also, contemplated is an adaptation in which muscular paralytics are utilized to minimize muscular co-contraction. Also, the devices and systems of the present invention can be adapted to provide better visualization of the current waveform delivered to the patient for example by displaying same using the control unit.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A portable negative pressure ventilation apparatus comprising
    a monitoring and sensing means operably coupled to a body, for monitoring and sensing a characteristic of the body or bodily function and providing an output signal(s) representative of the sensed characteristic;
    an electrode patch including a body attachment structure and a multiplicity of electrodes that are mechanically attached to the body attachment structure so as to be in a predetermined orientation, the body attachment being configured and arranged so as to be removably secured to the body;
    a control device that is operably coupled to each of the sensing means and the electrodes, the control device being configured and arranged to initially and automatically localize the phrenic nerve with respect to a given set of electrodes that is effective, when appropriately energized, for stimulating the phrenic nerve so as to establish negative pressure induced respiration in the body, said determination being based on the output signal(s) from the monitoring and sensing means;
    the control device being further configured and arranged so as to repetitively output stimulation signals via the given set of electrodes when such a determination is made by the control device, thereby continuously stimulating negative pressure induced respiration in the body.

2. The negative pressure ventilation device of claim 1, wherein:
    the monitoring and sensing means continues monitoring and sensing of the characteristic of the body or bodily function as the control device is continuously stimulating negative pressure induced respiration in the body and provides output signals to the control devices representative of the sensed characteristic; and
    wherein the control device is further configured and arranged to continuously monitor such output signals from the monitoring and sensing means and to one of control the stimulation signals being outputted so as to modify the negative pressure conditions being induced in the body for stimulation or to provide an indication to a user of an unsatisfactory condition.

3. The negative pressure ventilation device of claim 1, further including an alarm for providing one of an auditory or visual signal to a user and wherein the control device is further configured and arranged so as to output a signal to activate the alarm when the control device is unable to initially determine the given set of electrodes.

4. The negative pressure ventilation device of claim 3, wherein the control device is further configured and arranged so that the signal to activate the alarm is outputted to provide the indication of the unsatisfactory condition.

5. The negative pressure ventilation device of claim 1, wherein said control device is further configured and arranged to include a module that initially and automatically determines the given set of electrodes from the arrangement of the multiplicity of electrodes, said module including means for selectively energizing arrays of given electrodes with stimulation signals and for determining from said selective energizing which array(s) of electrode array establish negative pressure induced respiration, where one of the determined arrays is identified as the given set of electrodes.

6. The negative pressure ventilation device of claim 1, wherein said control device is further configured and arranged to include a module including processing circuitry and a program for execution on the processing circuitry for initially and automatically localize the phrenic nerve with respect to the given set of electrodes;

wherein the program includes instructions, criteria and code segments for:

selecting one subset array of electrodes from a predetermined number of subset arrays of the multiplicity of electrodes, energizing the selected subset array of electrodes with stimulation signals, evaluating the output signal from the monitoring and sensing means for the energized selected subset array and determining if the output signal indicates the presence of negative pressure induced respiration in the body, in the case where said evaluating and determining does not indicate the presence of negative pressure induced respiration, selecting another subset array of electrodes from the predetermined number of subset arrays, and repeating said energizing and evaluating; and in the case where said evaluating and determining does indicate the presence of negative pressure induced respiration:

identifying the selected subset array of electrodes or selected another subset array resulting in such an indication as the given set of electrodes, and thereafter repetitively energizing such given electrodes with stimulation signals so as to thereby continuously stimulate negative pressure induced respiration in the body.

7. The negative pressure ventilation device of claim 6, wherein the program further includes instructions, criteria and code segments for:

requesting a user to input specific patient information; and selecting one or more characteristics of the stimulation signal used for energizing each subset array and the given set of electrodes based on the inputted specific patient information.

8. The negative pressure ventilation device of claim 7, wherein:

the specific patient information relates to age and body type of the patient; and the module includes a database having a plurality operational characteristics for stimulation signals, the plurality of operational characteristics being related to different age ranges and a body types; and said selecting includes selecting the stimulation signal operational characteristic(s) whose age range and body type corresponds to the inputted specific patient information.

9. The negative pressure ventilation device of claim 1, wherein the electrodes are configured so that a proximal end portion of each electrode forms a needle like structure and having a length sufficient so that the proximal end of the proximal end portion extend through a portion of the skin.

10. A device kit for a medical emergency used for inducing respiration in a patient unable to breath on their own, said device kit including at least one electrode patch including a body attachment structure and a multiplicity of electrodes that are mechanically attached to the body attachment structure so as to be in a predetermined orientation, the body attachment being configured and arranged so as to be removably secured to the body;

a monitoring and sensing means for monitoring and sensing a characteristic of the body or bodily function and providing an output signal(s) representative of the sensed characteristic when operably coupled to the body;

a control device configured so as to be operably coupled to each of the sensing means and the electrodes, the control device being configured and arranged to:

initially and automatically localize the phrenic nerve with respect to a given set of electrodes that is effective, when appropriately energized, for stimulating the phrenic nerve so as to establish negative pressure induced respiration in the body, said determination being based on the output signal(s) from the monitoring and sensing means, and repetitively output stimulation signals via the given set of electrodes when such a determination is made by the control device, thereby continuously stimulating negative pressure induced respiration in the body;

wherein the monitoring and sensing means continues monitoring and sensing of the characteristic of the body or bodily function while the control device continuously stimulates negative pressure induced respiration in the body and provides output signals to the control devices representative of the sensed characteristic; and wherein the control device is further configured and arranged to continuously monitor such output signals from the monitoring and sensing means and to one of control the stimulation signals being outputted so as to modify the negative pressure conditions being induced in the body for stimulation or to provide an indication to a user of an unsatisfactory condition.

11. A method for localizing a phrenic nerve located in the neck of a body; said method comprising the steps of:

providing an electrode patch including a multiplicity of electrodes that are in a predetermined orientation;

removably securing the electrode patch to the neck so that at least some of the electrodes are in general proximity to the phrenic nerve;

monitoring and sensing a characteristic of the body or bodily function and providing an output signal(s) representative of the sensed characteristic;

selecting one subset array of electrodes from a predetermined number of subset arrays of the multiplicity of electrodes, energizing the selected subset array of electrodes with stimulation signals, evaluating the output signal from the monitoring and sensing means for the energized selected subset array and determining if the output signal indicates the presence of negative pressure induced respiration in the body, in the case where said evaluating and determining does not indicate the presence of negative pressure induced respiration, selecting another subset array of electrodes from the predetermined number of subset arrays, and repeating said energizing and evaluating; and in the case where said evaluating and determining does indicate the presence of negative pressure induced respiration, identifying the selected subset array of electrodes or selected another subset array resulting in such an indication as the given set of electrodes that are localized to the phrenic nerve.

12. The method of claim 11, further comprising the steps of:
- requesting a user to input specific patient information; and
- wherein said energizing includes selecting one or more operational characteristics of the stimulation signal used for energizing based on the inputted specific patient information.

13. The method of claim 12, wherein:
- the specific patient information relates to age and body type of the body;
- said energizing further includes providing a database having a plurality operational characteristics for stimulation signals, the plurality of operational characteristics being related to different age ranges and a body types; and
- said selecting includes selecting the stimulation signal operational characteristic(s) whose age range and body type corresponds to the inputted specific patient information.

14. The method of claim 11, wherein:
- the provided electrodes are configured so that a proximal end portion of each electrode forms a needle like structure;
- and said localizing includes acting on the provided electrodes so that a proximal end of the proximal end portion extends through a portion of skin of the body and is disposed within the body.

15. A method for inducing negative pressure respiration in a body using a phrenic nerve located in the neck of a body; said method comprising the steps of:
- removably securing an electrode patch including a multiplicity of electrodes that are in a predetermined orientation to the neck so that at least some of the electrodes are in general proximity to the phrenic nerve;
- monitoring and sensing a characteristic of the body or bodily function and providing an output signal(s) representative of the sensed characteristic;
- localizing the phrenic nerve with respect to a given set of electrodes that is effective, when appropriately energized, for stimulating the phrenic nerve so as to establish negative pressure induced respiration in the body, said locating being based on the output signal(s) from the monitoring and sensing;
- repetitively outputting stimulation signals via the given set of electrodes when such a determination is made, thereby continuously stimulating negative pressure induced respiration in the body.

16. The method of claim 15, wherein said localizing phrenic nerve includes:
- selecting one subset array of electrodes from a predetermined number of subset arrays of the multiplicity of electrodes,
- energizing the selected subset array of electrodes with stimulation signals,
- evaluating the output signal from the monitoring and sensing for the energized selected subset array and determining if the output signal indicates the presence of negative pressure induced respiration in the body,
- in the case where said evaluating and determining does not indicate the presence of negative pressure induced respiration, selecting another subset array of electrodes from the predetermined number of subset arrays, and repeating said energizing and evaluating; and
- in the case where said evaluating and determining does indicate the presence of negative pressure induced respiration, identifying the selected subset array of electrodes or selected another subset array resulting in such an indication as the given set of electrodes that are localized to the phrenic nerve.

17. The method of claim 16, further comprising the step(s) of:
- requesting a user to input specific patient information, the specific patient information relating to at least age and body type of the body; and
- wherein said energizing includes:
- providing a database having a plurality operational characteristics for stimulation signals, the plurality of operational characteristics being related to different age ranges and a body types, and
- selecting an operational characteristic(s) of a given stimulation signal used for energizing whose related age range and body type corresponds to the inputted specific patient information.

18. The method of claim 15, wherein:
- the provided electrodes are configured so that a proximal end portion of each electrode forms a needle like structure;
- and said localizing includes acting on the provided electrodes so that a proximal end of the proximal end portion extends through a portion of skin of the body and is disposed within the body.

19. The method of claim 15, wherein:
- monitoring and sensing of the characteristic of the body or bodily function continues as stimulating signals are being repetitively outputted resulting in negative pressure induced respiration in the body and provides output signals representative thereof; and
- continuously monitoring such output signals and in response to such output signals to one of (a) control the stimulation signals being outputted so as to modify the negative pressure conditions being induced in the body for stimulation or (b) provide an indication to a user of an unsatisfactory condition.

20. The method of claim 19, further comprising the step(s) of:
- providing an alarm that generates one of an auditory or visual signal to the user; and
- activating the alarm when one of (a) said localizing cannot localize the phrenic nerve with respect to the given set of electrodes or (b) to indicate the presence of an unsatisfactory condition.

* * * * *